United States Patent

Hohlweg et al.

(10) Patent No.: US 6,277,991 B1
(45) Date of Patent: Aug. 21, 2001

(54) 1,3,8-TRIAZASPIRO[4.5]DECANONES WITH HIGH AFFINITY FOR OPIOID RECEPTOR SUBTYPES

(75) Inventors: Rolf Hohlweg, Kvistgaard; Brett Watson, Vaerlose; Christain Thomsen, Stroby, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/311,469

(22) Filed: May 13, 1999

Related U.S. Application Data

(60) Provisional application No. 60/091,012, filed on Jun. 26, 1998, provisional application No. 60/093,519, filed on Jul. 21, 1998, and provisional application No. 60/120,295, filed on Feb. 16, 1999.

(30) Foreign Application Priority Data

| May 20, 1998 | (DK) | 0711/98 |
| May 26, 1998 | (DK) | 00729/98 |
| May 18, 1998 | (DK) | 0681/98 |
| Jul. 10, 1998 | (DK) | 00927/98 |
| Jan. 29, 1999 | (DK) | 00111/99 |

(51) Int. Cl.$^7$ .......... A61K 38/05; A61K 31/41; A61K 31/4164; C07D 401/04
(52) U.S. Cl. .......... 546/20; 514/19; 514/20; 514/2; 514/247; 514/303; 514/506; 514/18; 546/18; 546/20
(58) Field of Search ........ 546/18, 20; 514/247, 514/303, 506, 2, 7, 18, 20, 19, 278

(56) References Cited

U.S. PATENT DOCUMENTS

| 3,238,216 | 3/1966 | Janssen | 260/293.4 |
| 3,723,441 | 3/1973 | Kaiser et al. | 260/293.57 |
| 3,863,011 | 1/1975 | Corbin | 424/267 |
| 3,923,993 | 12/1975 | Corbin | 424/267 |

FOREIGN PATENT DOCUMENTS

| 0 856 514 A1 | 8/1998 | (EP) . |
| 0 921 125 A1 | 6/1999 | (EP) . |
| 1043141 | 9/1966 | (GB) . |
| 1547597 | 6/1979 | (GB) . |
| 1547587 * | 6/1979 | (GB) . |
| WO 91/13622 | 9/1991 | (WO) . |
| WO 93/12789 | 7/1993 | (WO) . |

OTHER PUBLICATIONS

Rafael O.P. De Campos et al European journal of Pharmacology vol. 316 (Aug. 16, 1996) pp. 227–286.*
Margaret Clagett–Dame et al, Biochimica et Biophysics Acta, vol. 986, (Mar. 20, 1989) pp. 271–280.*

Goodman and gillman, Pharmacological Basis of Therapeutic, Ninth edition, p. 13, 1996.*

Chemical Abstracts, vol. 81, No. 5, p. 435 (1974).

Chemical Abstracts, vol. 78, No. 9, p. 523 (1973).

Chemical Abstracts, vol. 126, No. 24, p. 73 (1997).

Chemical Abstracts, vol. 70, No. 17, pp. 264–265 (1969).

Lanzilotti et al., J. Org. Chem., vol. 44, pp. 4809–4813 (1979).

* cited by examiner

*Primary Examiner*—Alan L. Rotman
*Assistant Examiner*—Rita Desai
(74) *Attorney, Agent, or Firm*—Reza Green, Esq.; Valeta A. Gregg, Esq.

(57) ABSTRACT

The present invention relates to the use of small organic compounds acting as opioid receptor ligands for the treatment of vasomotor disturbances. In particular the present invention relates to the use of triaza-spiro compounds of formula

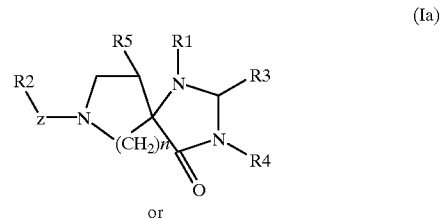

(Ia)

or

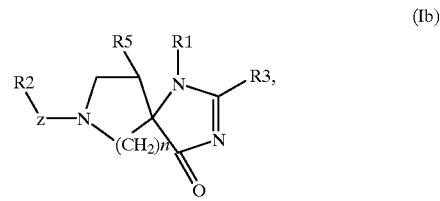

(Ib)

wherein $R^1, R^2, R^3, R^4, R^5$, z and n are defined in the specification, for the treatment of migraine, non-insulin dependent diabetes mellitus (type II diabetes), sepsis, inflammation, incontinence and/or vasomotor disturbances, in particular the peripheral vasomotor effects known as hot flushes or hot flashes.

38 Claims, No Drawings

1,3,8-TRIAZASPIRO[4.5]DECANONES WITH HIGH AFFINITY FOR OPIOID RECEPTOR SUBTYPES

CROSS-REFERENCE TO RELATED APPLICATIONS

This application claims priority under 35 U.S.C. 119 of U.S. provisional application Nos. 60/091,012 filed Jun. 26, 1998, 60/093,519 filed Jul. 21, 1998, 60/120,295 filed Feb. 16, 1999 and Danish application nos. 0681/98 filed May 18, 1998, 0711/98 filed May 20, 1998, 0729/98 filed May 26, 1998, 0927/98 filed Jul. 10, 1998 and 0111/99 filed Jan. 29, 1999, the contents of which are fully incorporated herein by reference.

FIELD OF INVENTION

The present invention relates to use of small organic compounds acting as opioid receptor ligands for the treatment of vasomotor disturbances. In particular the present invention relates to the compounds of formula Ia or Ib for the treatment of migraine, non-insulin dependent diabetes mellitus (type II diabetes), sepsis, inflammation, incontinence and/or vasomotor disturbances, in particular the peripheral vasomotor effects known as hot flushes or hot flashes. The present invention also embraces pharmaceutical compositions comprising these compounds and methods of using the compounds and their pharmaceutical compositions.

BACKGROUND OF THE INVENTION

A "hot flush" is a sudden transient sensation ranging from warmth to intense heat and typically accompanied by flushing and perspiration. It is the classic sign of the menopause and the predominant complaint of menopausal women. A positive correlation between plasma levels of calcitonin gene-related peptide (CGRP) and frequency of hot flushes in women has recently been reported (Chen et al., 1993, Lancet (342) 49), in accordance with the potent vasodilatory effect of CGRP (Brain et al., 1985, Nature, (313) 54–56). Also, a positive correlation between CGRP antagonists and diabetes, septic shock and inflammation has been described (Feurstein, G, Willette, R and Aiyar, N., 1995, Can. J. Physiol. Pharmacol. 73:1070–1074).

Recently, a novel heptadecapeptide, nociceptin, was discovered (Meunier et al., 1995, Nature (377) 532–535, Reinscheid et al., 1995, Science (270) 792–794). Nociceptin and analogues thereof have been disclosed in WO 97/07212, EP 813065 and in WO 97/07208. These peptides and inhibitors thereof are said to be useful for antagonizing physiologic effects of an opioid in an animal, and for treating/preventing a disease related to: hyperalgesia, neuroendocrine secretion, stress, locomotor activity, anxiety etc. Jenck, F et. al. also found, that Orphanin FQ acts as an anxiolytic to attenuate behavioral responses to stress (PNAS Vol. 94,1997). It is well known that triaza-spiro compounds are vasodilating agents and morphine-like analgesics as disclosed in U.S. Pat. Nos. 3,238,216 and 3,155,670 by Janssen.

SUMMARY OF THE INVENTION

It has been found that members of a novel group of triaza-spiro compounds have high affinity for nociceptin receptors which make them useful as regulators of peripheral vasomotor effects known as hot flushes. The present invention provides a compound of the formula Ia or Ib as disclosed below or a pharmaceutically acceptable salt thereof, for the preparation of a pharmaceutical composition for the treatment of Type II diabetes, septic shock, inflammation, incontinence and vasomotor disturbances, in particular the peripheral vasomotor effects known as hot flushes or hot flashes.

Further objects will become apparent from the following description.

DETAILED DESCRIPTION OF THE INVENTION

The present invention relates to use of a small organic compound acting as an opioid receptor ligand for the preparation of a pharmaceutical composition for the treatment of a disease selected from migraine, non-insulin dependent diabetes mellitus (type II diabetes), sepsis, inflammation, incontinence, vasomotor disturbances, in particular the peripheral vasomotor effects known as hot flushes or hot flashes and/or for alleviating symptoms of drug withdrawal, in particular abstinence symptoms occurring during withdrawal from abusive drugs.

In another aspect the invention relates to use of a small organic compound acting as a Nociceptin receptor ligand with a molecular weight of less than 1000 or a pharmaceutically acceptable salt thereof, for the preparation of a pharmaceutical composition for the treatment of vasomotor disturbances.

In still another aspect the invention relates to use of small organic compounds acting as Nociceptin receptor ligand with a molecular weight less than 600 or a pharmaceutically acceptable salt thereof, for the preparation of a pharmaceutical composition for the treatment of vasomotor disturbances.

In yet another aspect the invention relates to use of a small organic compound acting as a Nociceptin receptor ligand with less than 5 amide bonds or a pharmaceutically acceptable salt thereof, for the preparation of a pharmaceutical composition for the treatment of vasomotor disturbances.

In a further aspect the invention relates to use of a small organic compound acting as a Nociceptin receptor ligand wherein said compound has no amide bonds or a pharmaceutically acceptable salt thereof, for the preparation of a pharmaceutical composition for the treatment of vasomotor disturbances.

In still another aspect the invention relates to use of a compound wherein said compound comprises a triaza-spiro compound acting as a Nociceptin receptor ligand or a pharmaceutically acceptable salt thereof, for the preparation of a pharmaceutical composition for the treatment of vasomotor disturbances.

In yet another aspect the invention relates to use of a small organic compound acting as a Nociceptin receptor ligand with an $IC_{50}$ less than 1 $\mu$M or a pharmaceutically acceptable salt thereof, for the preparation of a pharmaceutical composition for the treatment of vasomotor disturbances.

In a second aspect the invention relates to a compound of formula

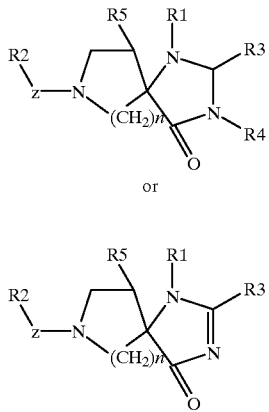

wherein

R¹ is phenyl, arylalkyl or thienyl, optionally substituted with one or more of halogene, cyano, nitro, trifluoromethyl, $C_{1-6}$-alkyl, hydroxy, $C_{1-6}$-alkoxy or $NR^6R^8$ wherein $R^6$ and $R^8$ independently are hydrogen or $C_{1-6}$-alkyl, or $R^1$ is $C_{1-6}$-alkyl;

$R^2$ is aminophenyl, $C_{1-6}$-monoalkylaminophenyl, $C_{1-6}$-dialkylaminophenyl, cyanophenyl, $C_{2-6}$-alkylphenyl, naphthyl, tetrahydronaphthyl, anthryl, furanyl, indanyl, indolyl, isoindolyl, benzothienyl, benzofuranyl, coumarinyl, said groups may be substituted with one or more of halogen, cyano, nitro, trifluoromethyl, $C_{1-6}$-alkyl, hydroxy, $C_{1-6}$-alkoxy, $C(O)R^7$, wherein $R^7$ is —OH, $C_{1-6}$-alkoxy or —$NR^{12}R^{13}$, wherein $R^{12}$ and $R^{13}$ independently are hydrogen or $C_{1-6}$-alkyl or $R^2$ is phenyl, phenoxy, benzodioxinyl or cyanodiphenylmethyl, any of which may be substituted with one or more of halogen, cyano, nitro, trifluoromethyl, $C_{1-6}$-alkyl, hydroxy, $C_{1-6}$-alkoxy, $C(O)R^7$, wherein $R^7$ is —OH, $C_1$-alkoxy or —$NR^{12}R^{13}$, wherein $R^{12}$ and $R^{13}$ independently are hydrogen or $C_{1-6}$ alkyl, provided that $R^1$ is not phenyl, $R^3$ is not methyl or hydrogen or $R^4$ is not hydrogen, acetyl, methyl, hydroxymethyl, ethyl, 2-cyanoethyl, propionyl or methoxymethyl;

$R^3$ is hydrogen, $C_{1-6}$-alkyl, phenyl, benzyl or acetyl;

$R^4$ is hydrogen or $(CH_2)_m$—$(CHR^9)$—$(CH_2)_p$-$AR^{11}$, wherein m and p independently are 0–4 and $R^9$ is hydrogen, $C_{1-6}$-alkyl, phenyl or arylalkyl, $R^{11}$ is $C_{1-6}$-alkyl, hydroxy, $C_{1-6}$-alkoxy, guanidino, an amino acid residue or a 2–4 peptidyl residue with a C-terminal group consisting of either $OCH_3$, or $NH_2$; $R^{11}$ can also be a group $NR^{14}R^{15}$ wherein $R^{14}$ and $R^{15}$ independently are hydrogen, $C_{1-6}$ alkyl, $(CH_2)qR^{16}$ where q can be 0 to 6 and $R^{16}$ can be a C3–C7 membered cycloalkyl ring, an optionally substituted aromatic or heteroaromatic ring, an aliphatic ring containing one or more heteroatoms, an alkoxy or aryloxy group, an amino or a guanidino group; A is —$CH_2$ or —C=O; provided that when $R^{11}$ is an amino acid or peptidyl residue, then A is a —C=O group;

$R^5$ is hydrogen or $C_{1-4}$-alkyl;

z is $CHR^{10}$ wherein $R^{10}$ is hydrogen, $C_{1-6}$-alkyl, phenyl or arylalkyl—or z is $C_{2-8}$-alkylene, $C_{2-8}$-alkenylene or $C_{2-8}$-alkynylene;

n is 1 or 2;

or a pharmaceutically acceptable salt thereof.

In another aspect of the invention $R^1$ is phenyl, arylalkyl or thienyl, optionally substituted with one or more of halogen, cyano, nitro, trifluoromethyl, $C_{1-6}$-alkyl, hydroxy, $C_{1-6}$-alkoxy or $NR^6R^8$ wherein $R^6$ and $R^8$ independently are hydrogen or $C_{1-6}$-alkyl, or $R^1$ is $C_{1-6}$-alkyl;

$R^2$ is aminophenyl, $C_{1-6}$-monoalkylaminophenyl, $C_{1-6}$-dialkylaminophenyl, cyanophenyl, $C_{2-6}$-alkylphenyl, naphthyl, tetrahydronaphthyl, furanyl, indanyl, benzothienyl, benzofuranyl, said groups may be substituted with one or more of halogen, cyano, nitro, trifluoromethyl, $C_{1-6}$-alkyl, hydroxy, $C_{1-6}$-alkoxy, $C(O)R^7$, wherein $R^7$ is —OH, —$NR^{12}R^{13}$, wherein $R^{12}$ and $R^{13}$ independently are hydrogen or $C_{1-6}$ alkyl, or $C_{1-6}$-alkoxy or $R^2$ is phenyl provided that $R^1$ is not phenyl, $R^3$ is not methyl or hydrogen and $R^4$ is not hydrogen, acetyl, methyl, hydroxymethyl, ethyl, 2-cyanoethyl, propionyl or methoxymethyl;

$R^3$ is hydrogen, $C_{1-6}$-alkyl, phenyl, benzyl or acetyl;

$R^4$ is hydrogen or $(CH_2)_m$—$(CHR^9)$—$(CH_2)p$-$AR^{11}$, wherein m and p independently are 0–4 and $R^9$ is hydrogen, $C_{1-6}$-alkyl, phenyl or arylalkyl, $R^{11}$ is $C_{1-6}$-alkyl, hydroxy, $C_{1-6}$-alkoxy, guanidino, an amino acid residue or a 2–4 peptidyl residue with a C-terminal group consisting of either $OCH_3$, or $NH_2$; $R^{11}$ can also be a group $NR^{14}R^{15}$ wherein $R^{14}$ and $R^{15}$ independently are hydrogen, $C_{1-6}$ alkyl, $(CH_2)qR^{16}$ where q can be 0 to 6 and $R^{16}$ can be a C3–C7 membered cycloalkyl ring, an optionally substituted aromatic or heteroaromatic ring, an aliphatic ring containing one or more heteroatoms, an alkoxy or aryloxy group, an amino or a guanidino group; A is —$CH_2$ or —C=O; provided that when $R^{11}$ is an amino acid or peptidyl residue, then A is a —C=O group;

$R^5$ is hydrogen or C-alkyl;

z is $CHR^{10}$ wherein $R^{10}$ is hydrogen, $C_{1-6}$-alkyl, phenyl or arylalkyl—or z is $C_{2-8}$-alkylene, $C_{2-8}$-alkenylene or $C_{2-8}$-alkynylene;

n is 1 or 2;

or a pharmaceutically acceptable salt thereof.

In another embodiment of the invention $R^1$ is $C_{1-6}$-alkyl, phenyl, arylalkyl or thienyl.

In yet another embodiment of the invention $R^2$ is aminophenyl, $C_{1-6}$-monoalkylaminophenyl, $C_{1-6}$-dialkylaminophenyl, cyanophenyl, $C_{2-6}$-alkylphenyl, naphthyl, tetrahydronaphthyl, furanyl, indanyl, benzothienyl, benzofuranyl, said groups may be substituted with one or more of halogen, cyano, nitro, trifluoromethyl, $C_{1-6}$-alkyl, hydroxy, $C_{1-6}$-alkoxy, $C(O)R^7$, wherein $R^7$ is —OH, —$NR^{12}R^{13}$, wherein $R^{12}$ and $R^{13}$ independently are hydrogen or $C_{1-6}$ alkyl, or $C_{1-6}$-alkoxy.

In still another embodiment of the invention $R^2$ is cyanophenyl or naphthyl, said groups may be substituted with one or more of fluorine, chlorine, bromine, cyano, nitro, trifluoromethyl, $C_{1-6}$-alkyl, hydroxy, $C_{1-6}$-alkoxy, $C(O)R^7$, wherein $R^7$ is —OH, $C_{1-6}$-alkoxy or —$NR^{12}R^{13}$ wherein $R^{12}$ and $R^{13}$ independently are hydrogen or $C_{1-6}$ alkyl.

In a preferred embodiment of the invention n is 2.

Another preferred embodiment of the invention comprises compound Ia wherein $R^1$, $R^2$, $R^3$, $R^4$, $R^5$, z and n are defined as above.

In still another preferred embodiment of the invention $R^1$ is phenyl.

In yet another preferred embodiment of the invention the compounds are selected from the following:

(4-Oxo-8-phenethyl-1-phenyl-1,3,8-triaza-spiro[4.5]dec-3-yl)-acetic acid methyl ester, (1a)

{8-[2-(1,3-Dioxo-1,3-dihydro-isoindol-2-yl)-ethyl]-4-oxo-1-phenyl-1,3,8-triaza-spiro[4.5]dec-3-yl}-acetic acid methyl ester, (1b)
[8-(3-Cyano-3,3-diphenyl-propyl)-4-oxo-1-phenyl-1,3,8-triaza-spiro[4.5]dec-3-yl]-acetic acid methyl ester, (1c)
[8-(4-Nitro-benzyl)-4-oxo-1-phenyl-1,3,8-triaza-spiro[4.5]dec-3-yl]-acetic acid methyl ester, (1d)
[4-Oxo-1-phenyl-8-(3-phenyl-propyl)-1,3,8-triaza-spiro[4.5]dec-3-yl]-acetic acid methyl ester, (1e)
[4-Oxo-8-(3-phenoxy-propyl)-1-phenyl-1,3,8-triaza-spiro[4.5]dec-3-yl]-acetic acid methyl ester, (1f)
[4-Oxo-8-(4-phenoxy-butyl)-1-phenyl-1,3,8triaza-spiro[4.5]dec-3-yl]-acetic acid methyl ester, (1g)
[8-(2,3-Dihydro-benzo[1,4]dioxin-2-ylmethyl)-4-oxo-1-phenyl-1,3,8-triaza-spiro[4.5]dec-3-yl]-acetic acid methyl ester, (1h)
{8-[5-(1,3-Dioxo-1,3-dihydro-isoindol-2-yl)-pentyl]-4-oxo-1-phenyl-1,3,8-triaza-spiro[4.5]dec-3-yl}acetic acid methyl ester, (1i)
(8-Naphthalen-1ylmethyl-4-oxo-1-phenyl-1,3,8-triaza-spiro[4.5]dec-3-yl)-acetic acid methyl ester, (1j)
{8-[2-(4-Fluoro-phenoxy)ethyl]-4-oxo-1-phenyl-1,3,8-triaza-spiro[4.5]dec-3-yl}-acetic acid methyl ester, (1k)
[8-(6,7-Dimethoxy-2-oxo-2H-chromen-4-ylmethyl)-4-oxo-1-phenyl-1,3,8-triaza-spiro[4.5]dec-3-yl]-acetic acid methyl ester, (1l)
[8-(2-Naphthalen-1-yl-ethyl)-4-oxo-1-phenyl-1,3,84triaza-spiro[4.5]dec-3-yl]-acetic acid methyl ester, (1m)
[8-(3-Cyano-benzyl)-4-oxo-1-phenyl-1,3,8-triaza-spiro[4.5]dec-3-yl]-acetic acid methyl ester, (1n)
3-(3-Methoxycarbonylmethyl-4-oxo-1-phenyl-1,3,8-triaza-spiro[4.5]dec-8-ylmethyl)-benzoic acid methyl ester, (1o)
[8-(4-Bromo-benzyl)-4-oxo-1-phenyl-1,3,8-triaza-spiro[4.5]dec-3-yl]-acetic acid methyl ester, (1p)
[8(3,4-Dichloro-benzyl)-4-oxo-1-phenyl-1,3,8-triaza-spiro[4.5]dec-3yl]-acetic acid methyl ester, (1q)
(8-Anthracen-9-ylmethyl-4-oxo-1-phenyl-1,3,8-triaza-spiro[4.5]dec-3-yl)-acetic acid methyl ester, (1r)
5-Guanidino-2-(S)-[2-(8-naphthalen-1-ylmethyl-4-oxo-1-phenyl-1,3,8-triaza-spiro[4.5]dec-3-yl)-acetylamino] pentanoic acid methylester,
N-(2-Guanidino-ethyl)-2-(8-naphthalen-1-ylmethyl-4-oxo-1-phenyl-1,3,8-triaza-spiro[4.5]dec-3-yl)-acetamide,
3-(7-Amino-heptyl)-8-naphthalen-1-ylmethyl-1-phenyl-1,3,8-triaza-spiro[4.5]decan-4-one,
3-(1H-Imidazol-4-yl)-2-(S)-[2-(8-naphthalen-1-ylmethyl-4-oxo-1-phenyl-1,3,8-triaza-spiro[4.5]dec-3yl)-acetyiamino]-propionamide,
5-Guanidino-2-(S)-[2-(8-naphthalen-1-ylmethyl-4-oxo-1-phenyl-1,3,8-triaza-spiro[4.5]dec-3-yl)-acetylamino]-pentanoic acid amide,
5-Guanidino-2-(R)-[2-(8-naphthalen-1-ylmethyl-4-oxo-1-phenyl-1,3,8-triaza-spiro[4.5]dec-3-yl)-acetylamino]-pentanoic acid amide,
N-(3-Guanidino-propyl)-2-(8-naphthalen-1-ylmethyl-4-oxo-1-phenyl-1,3,8-triaza-spiro[4.5]dec-3-yl)-acetamide,
3-(5-Amino-pentyl)-8-naphthalen-1-ylmethyl-1-phenyl-1,3,8-triaza-spiro[4.5]decan-4-one,
N-(3-Amino-propyl)-2-(8-naphthalen-1-ylmethyl-4-oxo-1-phenyl-1,3,8-triaza-spiro[4.5]dec-3-yl)-acetamide,
N-(2-Amino-ethyl)-2-(8-naphthalen-1-ylmethyl-4-oxo-1-phenyl-1,3,8-triaza-spiro[4.5]dec-3-yl)-acetamide,
N-[7-(8-Naphthalen-1-ylmethyl-4-oxo-1-phenyl-1,3,8-triaza-spiro[4.5]dec-3-yl)-heptyl]guanidine,
3-Ethyl-8-naphthalen-1-ylmethyl-1-phenyl-1,3,8-triaza-spiro[4.5]decan-4-one,
2-(8-Naphthalen-1-ylmethyl-4-oxo-1-phenyl-1,3,8-triaza-spiro[4.5]dec-3-yl)-N-(tetrahydro-furan-2-ylmethyl)-acetamide,
2-(8-Naphthalen-1-ylmethyl-4-oxo1-phenyl-1,3,8-triaza-spiro[4.5]dec-3-yl)-N-[3-(2-oxo-pyrrolidin-1-yl)-propyl]-acetamide,
6-Amino-2-(S)-[2-(8naphthalen-1-ylmethyl-4-oxo-1-phenyl-1,3,8-triaza-spiro[4.5]dec-3-yl)-acetylamino]-hexanoic acid amide,
N-Carbamoylmethyl-2-(8-naphthalen-1-ylmethyl-4-oxo-1-phenyl-1,3,8-triaza-spiro[4.5]dec-3-yl)-acetamide,
2-(S)-[2-(8-Naphthalen-1-ylmethyl-4-oxo-1-phenyl-1,3,8-triaza-spiro[4.5]dec-3-yl)-acetylamino]-phenyl-acetamide,
6-Amino-2-(S)-(2-{6-amino-2-(S)-[2-(8-naphthalen-1-ylmethyl-4-oxo-1-phenyl-1,3,8-triaza-spiro[4.5]dec-3-yl)-acetylamino]-hexanoylamino}-acetylamino)-hexanoic acid amide,
5-Guanidino-2-(S)-{2-[2-(8-naphthalen-1-ylmethyl-4-oxo-1-phenyl-1,3,8-triaza-spiro[4.5]dec-3-yl)-acetylamino]-acetylamino}pentanoic acid amide or
5-Guanidino-2-(S)-(2-{2-[2-(8-naphthalen-1-ylmethyl-4-oxo-1-phenyl-1,3,8-triaza-spiro[4.5]dec-3-yl)-acetylamino]-acetylamino)-acetylamino}-pentanoic acid amide.

In a most preferred embodiment of the invention the compounds are selected from the following:
(4-Oxo-8-phenethyl-1-phenyl-1,3,8-triaza-spiro[4.5]dec-3-yl)-acetic acid methyl ester,
[8-(2-Naphthalen-1-yl-ethyl)-4-oxo-1-phenyl-1,3,8-triaza-spiro[4.5]dec-3-yl]-acetic acid methyl ester,
[8-(4-Bromo-benzyl)-4-oxo-1-phenyl-1,3,8-triaza-spiro[4.5]dec-3-yl]-acetic acid methyl ester,
[8-(3,4-Dichloro-benzyl)-4-oxo-1-phenyl-1,3,8-triaza-spiro[4.5]dec-3-yl]-acetic acid methyl ester,
5-Guanidino-2-(S)-[2-(8-naphthalen-1-ylmethyl-4-oxo-1-phenyl-1,3,8-triaza-spiro[4.5]dec-3-yl)-acetylamino]-pentanoic acid amide,
5-Guanidino-2-(R)-[2-(8-naphthalen-1-ylmethyl-4-oxo-1-phenyl-1,3,8-triaza-spiro[4.5]dec-3-yl)-acetylamino]-pentanoic acid amide or
3-(7-Amino-heptyl)-8-naphthalen-1-ylmethyl-1-phenyl-1,3,8-triaza-spiro[4.5]decan-4-one.

In a third aspect the invention comprises use of a compound of formula

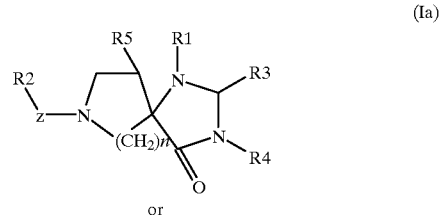

(Ia)

or

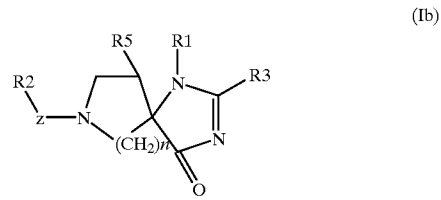

(Ib)

wherein
R$^1$ is phenyl, arylalkyl or thienyl, optionally substituted with one or more of halogen, cyano, nitro, trifluoromethyl, C$_{1-6}$-alkyl, hydroxy, C$_{1-6}$-alkoxy or NR$^6$R$^8$ wherein R$^6$ and R$^8$ independently are hydrogen or C$_{1-6}$-alkyl, or R$^1$ is C$_{1-6}$-alkyl;

R² is phenyl, phenoxy, benzodioxinyl, cyanodiphenylmethyl, aminophenyl, $C_{1-6}$-monoalkylaminophenyl, $C_{1-6}$-dialkylaminophenyl, naphthyl, tetrahydronaphthyl, anthryl, furanyl, indanyl, indolyl, isoindolyl, benzothienyl, benzofuranyl, coumarinyl, said groups may be substituted with one or more of halogen, cyano, nitro, trifluoromethyl, $C_{1-6}$-alkyl, hydroxy, alkoxy, C(O)R⁷, wherein R⁷ is —OH, $C_{1-6}$-alkoxy or —NR¹²R₁₃, wherein R¹² and R¹³ independently are hydrogen or $C_{1-6}$ alkyl;

R³ is hydrogen, $C_{1-6}$-alkyl, phenyl, benzyl or acetyl;

R⁴ is hydrogen or $(CH_2)_m$—(CHR⁹)—$(CH_2)$p-AR¹¹, wherein m and p independently are 0–4 and R⁹ is hydrogen, $C_{1-6}$-alkyl, phenyl or arylalkyl, R¹¹ is $C_{1-6}$-alkyl, hydroxy, $C_{1-6}$-alkoxy, guanidino, an amino acid residue or a 2–4 peptidyl residue with a C-terminal group consisting of either OCH₃, or NH₂; R¹¹ can also be a group NR¹⁴R¹⁵ wherein R¹⁴ and R¹⁵ independently are hydrogen, $C_{1-6}$ alkyl, $(CH_2)$qR¹⁶ where q can be 0 to 6 and R¹⁶ can be a C3–C7 membered cycloalkyl ring, an optionally substituted aromatic or heteroaromatic ring, an aliphatic ring containing one or more heteroatoms, an alkoxy or aryloxy group, an amino or a guanidino group; A is —CH₂ or —C═O; provided that when R¹¹ is an amino acid or peptidyl residue, then A is a —C═O group; or R⁵ is hydrogen or $C_{1-4}$-alkyl;

z is CHR¹⁰ wherein R¹⁰ is hydrogen, $C_{1-6}$-alkyl, phenyl or arylalkyl—or z is $C_{2-8}$-alkylene, $C_{2-8}$-alkenylene or $C_{2-8}$-alkynylene;

n is 1 or 2 or a pharmaceutically acceptable salt thereof for the treatment of migraine, non-insulin dependent diabetes mellitus (type II diabetes), sepsis, inflammation, incontinence and/or vasomotor disturbances, in particular the peripheral vasomotor effects known as hot flushes or hot flashes.

In another embodiment of the invention the composition is in a form suitable for oral, nasal, transdermal, pulmonal, or parenteral administration.

In a further embodiment of the present invention the compound of the formula Ia or Ib is administered as a dose in the range from about 0.01 to about 5000 mg per patient per day, preferably from about 1 to about 1000 mg per patient per day, especially from about 10 to about 100 mg per patient per day, e.g. about 100 mg per patient per day.

In a fourth aspect the invention relates to a method for the treatment or prevention of migraine, Type II diabetes, sepsis, inflammation, incontinence and/or vasomotor disturbances, in particular the peripheral vasomotor effects known as hot flushes or hot flashes, the method comprising administering to a patient in need thereof an effective amount of a compound of formula Ia or Ib or a pharmaceutically acceptable salt thereof.

In a fifth aspect the invention relates to a pharmaceutical composition comprising triaza-spiro compounds with high affinity to the nociceptin receptor, or a pharmaceutically acceptable salt thereof.

In a sixth aspect the invention relates to a method of treating symptoms of drug withdrawal, in particular abstinence symptoms occurring during withdrawal from abusive drugs.

The effective, such as the therapeutically effective amount of a compound of the formula Ia or Ib, will depend upon the mode of administration, on the therapy desired, form in which administered, the subject to be treated and the body weight of the subject to be treated, and the preference and experience of the physician or veterinarian in charge.

As used herein the term "patient" comprises any mammal which may benefit from treatment or prevention of vasomotor disturbances, such as a human, especially if the mammal is a female, such as a woman. However, "patient" is not intended to be limited to a woman.

As used herein the term "small organic compounds" refers to compounds with a molecular weight below 1000 and with less than 5 amide bonds or no amide bonds.

As used herein the term "triaza-spiro" represents a compound of formula

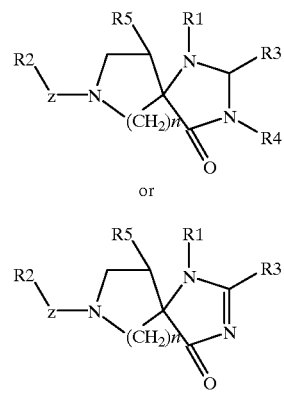

or with various substituents as defined above.

As used herein the term "high affinity" represents an IC₅₀ below 1 μM.

As used herein the term "arylalkyl" refers to a straight or branched saturated carbon chain containing from 1 to 6 carbons substituted with an aromatic hydrocarbon; such as benzyl, phenethyl, 3-phenylpropyl, 1-naphtylmethyl, 2-(1-naphtyl)ethyl and the like.

As used herein the term "$C_{1-6}$-alkyl" represent a branched or straight alkyl group or cycloalkyl with five or six carbon in the ring. Typical $C_{1-6}$-alkyl groups include, but are not limited to, methyl, ethyl, n-propyl, iso-propyl, butyl, iso-butyl, sec-butyl, tert-butyl, pentyl, iso-pentyl, hexyl, iso-hexyl and the like.

As used herein the term "$C_{1-6}$-alkoxy" alone or in combination is intended to include those $C_{1-6}$-alkyl groups of the designated length in either a linear or branched or cyclic configuration linked through an ether oxygen having its free valence bond from the ether oxygen. Examples of linear alkoxy groups are methoxy, ethoxy, propoxy, butoxy, pentoxy and hexoxy. Examples of branched alkoxy are isopropoxy, sec-butoxy, tert-butoxy, isopentoxy and isohexoxy. Examples of cyclic alkoxy are cyclopropyloxy, cyclobutyloxy, cyclopentyloxy and cyclohexyloxy.

As used herein the term "halogen" means fluorine, chlorine, bromine or iodine.

As used herein the term "amino acid residue or peptidyl residues" is also meant to comprise naturally occurring or synthetically produced amino acids linked to the compound by an amide bond.

As used herein the terms "$C_{2-8}$-alkylene" represent a branched or straight alkyl group having from one to the specified number of carbon atoms. Typical $C_{2-8}$-alkylene groups include, but are not limited to, ethylene, n-propylene, iso-propylene, butylene, iso-butylene, sec-butylene, tert-butylene, pentylene, iso-pentylene, hexylene, iso-hexylene and the like.

As used herein the terms "$C_{2-8}$-alkenylene" represents an olefinically unsaturated branched or straight group with at least one double bond. Examples of such groups include, but are not limited to, vinyl, 1-propenylene, allylene, isopropenylene, 1,3-butadienylene, 1-butenylene, hexenylene, pentenylene, and the like.

As used herein the terms "$C_{2-8}$-alkynylene" represent an unsaturated branched or straight group having at least one triple bond. Examples of such groups include, but are not limited to, 1-propynylene, 1-butynylene, 2-butynylene, 1-pentynylene, 2-pentynylene and the like.

As used herein the term "ligand" is also meant to comprise a compound with agonistic, partial agonistic or antagonistic activity specifically binding to receptor proteins.

As used herein the term "treatment" is also meant to comprise prophylactic treatment.

The preparation of compounds of formula Ia may include, but are not limited to the following methods:

A:

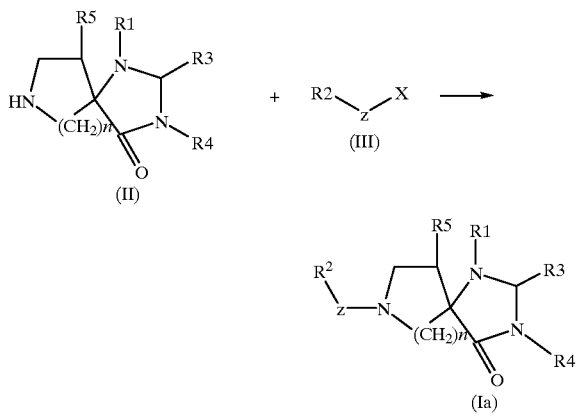

A compound of formula (II) wherein $R^1$, $R^3$, R $R^5$ and n are as defined above may be allowed to react with a compound of formula (III), wherein $R^2$ and z are defined as above and X is a suitable leaving group such as halogen, p-toluene sulfonate or mesylate. This alkylation reaction may be carried out in a solvent such as acetone, dibutylether, 2-butanone, methyl ethyl ketone, ethyl acetate, tetrahydrofuran (THF) or toluene in the presence of a base e.g. sodium hydride and a catalyst, e.g. an alkali metal iodide at a temperature up to reflux temperature for the solvent used for e.g. 1 to 120 h. Compounds of formula (II) may be prepared by known methods, e.g. as described in U.S. Pat. No. 3,238,216. Compounds of formula (III) are commercially available or may readily be prepared by methods familiar to those skilled in the art.

B:

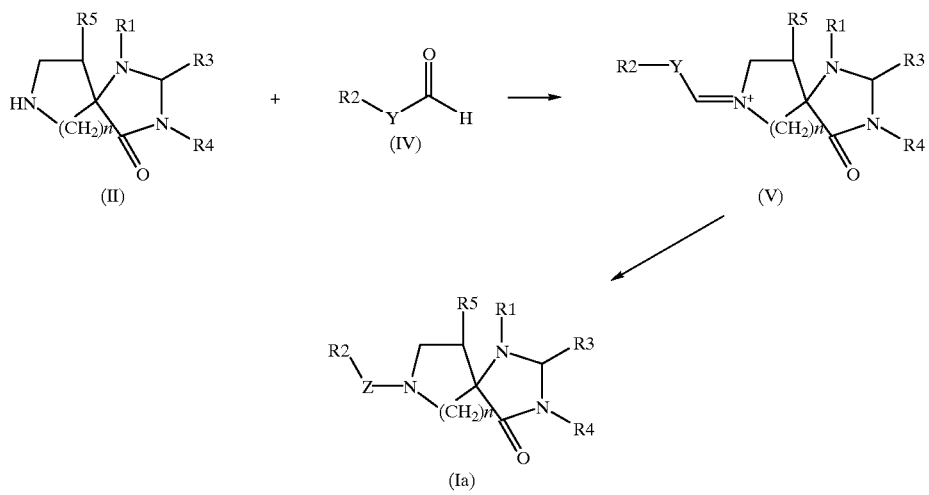

A compound of formula (II) wherein $R^1$, $R^3$, $R^4$ $R^5$, and n are as defined above may be allowed to react with an aldehyde of formula (IV), wherein $R^2$ is as defined above and the linker y is one C-atom shorter than linker z, where z is as defined above, to form an imine of formula (V). The reaction may be carried out in a suitable solvent like a lower aliphatic alcohol such as e.g. ethanol or an ether such as e.g. tetrahydrofuran or a mixture of these. In a second step, the formed iminium derivative of formula (V) is then reduced to an amine of formula (Ia) by the addition of a suitable reducing agent, e.g. a hydride as sodium cyanoborohydride or sodium borohydride in e.g. 1 to 120 h at 20° C. to reflux temperature. Compounds of formula (Ia) may also be prepared in a parallel fashion using solid phase technology, e.g. as described by F. Zaragoza and S. V. Petersen, Tetrahedron, 52, 10823 (1996). In this case, $R^4$ in a compound of formula (II) is replaced by $(CH_2)_m$—$(CHR^9)$—$(CH_2)_p$—$C(O)R^{7b}$, wherein m, p and $R^9$ are as defined above and $R^{7b}$ is a resin-O— or a resin-NH-residue. The above described reactions are followed by a cleavage from the resin to form a compound of formula (Ia). The cleavage conditions used depend on the type of resin used and are commonly known to those skilled in the art.

C:

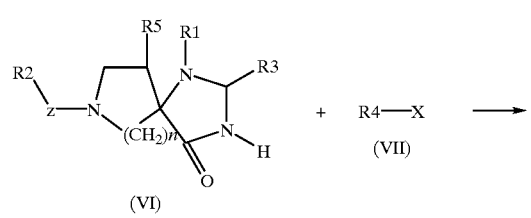

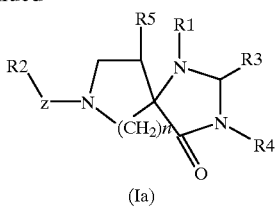

(Ia)

A compound of formula (VI) wherein $R^1$, $R^2$, $R^3$, $R^5$, z and n are as defined above, may be deprotonated at N3 with a suitable base, as sodium hydride, n-butyl lithium or potassium tert.-butoxide in an aprotic solvent as e.g. dimethyl formamide or dimethylsulfoxide and subsequently allowed to react with a reagent of formula (VII), wherein $R^4$ and X are as defined above. The reaction may be carried out at temperatures from 0° C. to reflux temperature, preferably at room temperature in 1 to 24 hours, to form a compound of formula (Ia).

D:

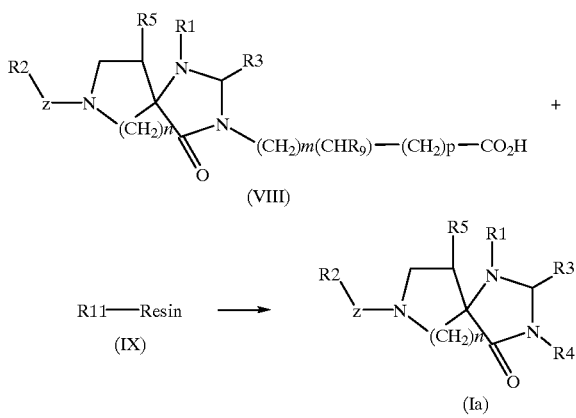

A compound of formula (Ia) may further be synthesized by allowing a compound of formula (VIII), wherein $R^1$, $R^2$, $R^3$, $R^5$, $R^9$, m, p, n an z are as described above, to react with a compound of formula (IX), in which the $R^{11}$ group bears a residue which is coupled to a resin and may be subsequently cleaved from the resin as an ester or amide moiety. The coupling reaction between (VIII) and (IX) may be carried out in a suitable solvent as e.g. dimethyl formamide or N-methyl pyrrolidone using e.g. a coupling reagent from the class of the carbodiimides, a benzotriazol and an optional base as a hindered tertiary amine. These amide couplings are well documented in the literature and commonly known. Compounds of formula (IX) may be commercially available resins, or can be prepared from such commercially available resins using general alkylation, reductive amination, or acylation methods.

Within the present invention, the compound of the formula Ia or Ib may be prepared in the form of pharmaceutically acceptable salts such as base or acid addition salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, maleic acid, tartaric acid, citric acid, benzoic acid, salicylic acid and the like. Suitable inorganic acid-addition salts include salts of hydrochloric, hydrobromic, sulfuric and phosphoric acids and the like. Further examples of pharmaceutically accept-able inorganic or organic acid addition salts include the pharmaceutically acceptable salts listed in *Journal of Pharmaceutical Science,* 66, 2 (1977) which are known to the skilled artisan.

Also intended as pharmaceutically acceptable acid addition salts are the hydrates which the present compound of the formula Ia or Ib are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the formula Ia or Ib of this invention may form solvates with standard low molecular weight solvents using methods known to a person skilled in the art.

The compound of the formula Ia or Ib may be administered in pharmaceutically acceptable acid addition salt form. Such salt forms are believed to exhibit approximately the same order of activity as the free base forms.

A pharmaceutical composition for use in accordance with the present invention comprises, one or more compound of the formula Ia or Ib as active ingredient(s), or a pharmaceutically acceptable salt thereof together with a pharmaceutically acceptable carrier or diluent.

Pharmaceutical compositions containing compounds of the formula Ia or Ib of the present invention may be prepared by conventional techniques, e.g. as described in *Remington: The Science and Practise of Pharmacy.* 19$^{th}$ Ed., 1995. The compositions may appear in conventional forms, for example capsules, tablets, aerosols, solutions, suspensions or topical applications.

Typical compositions include Compound of formula Ia or Ib or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatin, lactose, terra alba, sucrose, cyclodextrin, amylose, magnesium stearate, talc, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment.

If a solid carrier is used for oral administration, the preparation may be tableted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula Ia or Ib dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cydodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 100 mg |
| Colloidal silicon dioxide (AEROSIL) | 1.5 mg |
| Cellulose, microcryst. (AVICEL) | 70 mg |
| Modified cellulose gum (AC-DI-SOL) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

Any novel feature or combination of features described herein is considered essential to this invention.
Pharmacological Effects Male Sprague Dawley rats (300±25 g) were anesthetized with pentobarbital sodium (50 mg/kg i.p.) and polyethylene catheters were positioned in both femoral veins for the intravenous administration of drugs, such as nociceptin and analogues, and into the left femoral artery in order to measure arterial blood pressure and heart rate. The trachea was cannulated with polyethylene tubing and the rat was pithed, ventilated and drug treated as described by Nuki Y. et al. (Effects of Dorsal Rhizotomy on Depressor Response to Spinal Cord Stimulation Mediated by Endogenous Calcitonin Gene-related Peptide in the Pithed Rat. J. Neurosurg. 1993; 79:899–904).

EXAMPLES

The process for preparing compounds of formula Ia or Ib and preparations containing them is further illustrated in the following examples, which, however, are not to be construed as limiting.

Hereinafter, TLC is thin layer chromatography, $CDCl_3$ is deuterio chloroform and $DMSO-d_6$ is hexadeuterio dimethylsulfoxide. The structures of the compounds are confirmed by either elemental analysis or NMR, where peaks assigned to characteristic protons in the title compounds are presented where appropriate. $^1H$ NMR shifts ($\delta_H$) are given in parts per million (ppm). HPLC-MS analyses were performed on a PE Sciex API 100 LC/MS System using Method 1: a Waters™ 3 mm×150 mm 3.5 μ C-18 Symmetry column and positive ionspray with a flow rate of 20 μL/minute. The column was eluted with a linear gradient of 5–90% A, 85–0% B and 10% C in 15 minutes at a flow rate of 1 ml/min (solvent A=acetonitrile, solvent B=water and solvent C=0.1% trifluoroacetic acid in water). Method 2: a YMC ODS-A 120 Å s—5μ 3 mm×50 mm column and positive ionspray with a flow rate of 20 μL/minute. The column was eluted with a linear gradient of 5–90% A, 85–0% B and 10% C in 7.5 minutes at a flow rate of 1.5 ml/min.(solvent A=acetonitrile, solvent B=water and solvent C=0.5% trifluoroacetic acid in water). M.p. is melting point and is given in ° C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1

8-Alkylated 4-oxo-1-phenyl-1,3,8-triaza-spiro[4.5] dec-3-yl)-acetic acid methyl esters (Method A)

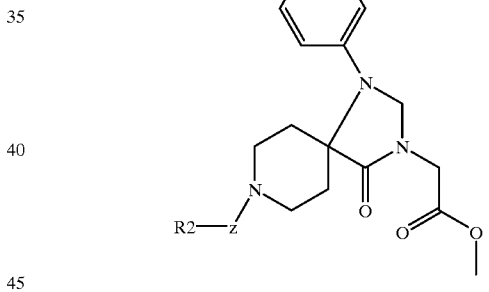

Wang resin (2.17 g, 2.0 mmol) was placed in a solid synthesis flask equipped with a glass frit and swelled in dry dimethylformamide (15 ml) for 15 minutes. The excess solvent was removed by suction and a solution of Fmoc-3-carboxymethyl-1-phenyl-1,3,8-triazaspiro[4.5]decan-4-one (2.05 g, 4.0 mmol) in dimethylformamide (8.0 ml) was added. The mixture was agitated for 5 minutes, dry pyridine (0.53 ml) and 2,6-dichlorobenzoyl chloride (0.54 ml, 4.0 mmol) was added and the mixture was agitated for 20 h. The solution was removed by suction and the resin was washed with dimethylformamide (2×10 ml) and 1,2-dichloroethane (4×10 ml). Dichloromethane (8 ml), pyridine (0.81 ml, 10 mmol) and benzoyl chloride (0.81 ml, 7.0 mmol) were added to the resin and the mixture was agitated for 2 h. The solution was removed by suction and the resin was washed with dichloroethane (4×10 ml), methanol (2×10 ml) and N,N-dimethylformamide (2×10 ml). To remove the Fmoc group, the resin was agitated with 20% piperidine in N,N-dimethylformamide (10 ml) for 30 minutes. The solution was removed by suction, the resin was washed with N,N-dimethylformamide (2×10 ml), dichloromethane (4×10 ml)

and methanol (3×10 ml) and dried. This yielded the Wang resin (2.53 g) with attached 3-carboxy-1-phenyl-1,3,8-triazaspiro[4.5]decan-4-one (0.67 mmol/g).

The following solid phase syntheses were carried out parallely using the apparatus described by F. Zaragoza and S. V. Petersen, Tetrahedron, 52, 10823 (1996). Equal portions of the above resin (67 mg, 0.045 mmol) were placed in Teflon tubes equipped with a frit on a mechanical shaker. Dimethyl sulfoxide (1 ml), the appropriate alkyl bromide $R^2$—z—x (0.225 mmol) and diisopropylethylamine (0.029 g, 0.225 mmol) were added to the resin. The tubes were heated to 60° C. and agitated for 16 h. The resin was drained, washed with dimethyl sulfoxide (2×1 ml), dichloromethane (4×1 ml) and methanol (2×1 ml). A solution of sodium methoxide (0.009 mmol) in a mixture of tetrahydrofuran/methanol 4:1 (2 ml) was added to the resin and the suspension was agitated at 50° C. for 16 h. The mixture was neutralized by addition of a solution of acetic acid (0.01 mmol) in a mixture of tetrahydrofuran/methanol 4:1 (1 ml), the solution was drained and the resin was washed with tetrahydrofuran (1 ml). The combined filtrates were concentrated in vacuo to yield the title compounds.

| Entry | Name | $R^2$-z-X | MW calculated | LC/MS MH+ | rt [min] (method) |
|---|---|---|---|---|---|
| 1a | (4-Oxo-8-phenethyl-1-phenyl-1,3,8-triaza-spiro[4.5]dec-3-yl)-acetic acid methyl ester | | 407.5 | 408.2 | 9.18 (1) |
| 1b | {8-[2-(1,3-Dioxo-1,3-dihydro-isoindol-2-yl)-ethyl]-4-oxo-1-phenyl-1,3,8-triaza-spiro[4.5]dec-3-yl}-acetic acid methyl ester | | 476.5 | 477.2 | 8.90 (1) |
| 1c | [8-(3-Cyano-3,3-diphenyl-propyl)-4-oxo-1-phenyl-1,3,8-triaza-spiro[4.5]dec-3-yl]-acetic acid methyl ester | | 522.7 | 523.0 | 11.03 (1) |
| 1d | [8-(4-Nitro-benzyl)-4-oxo-1-phenyl-1,3,8-triaza-spiro[4.5]dec-3-yl]-acetic acid methyl ester | | 438.5 | 439.2 | 9.43 (1) |
| 1e | [4-Oxo-1-phenyl-8-(3-phenyl-propyl)-1,3,8-triaza-spiro[4.5]dec-3-yl]-acetic acid methyl ester | | 421.5 | 422.2 | 9.77 (1) |

-continued

| Entry | Name | R²-z-X | MW calculated | LC/MS MH⁺ | rt [min] (method) |
|---|---|---|---|---|---|
| 1f | [4-Oxo-8-(3-phenoxy-propyl)-1-phenyl-1,3,8-triaza-spiro[4.5]dec-3-yl]-acetic acid methyl ester | | 437.5 | 438.2 | 9.85 (1) |
| 1g | [4-Oxo-8-(4-phenoxy-butyl)-1-phenyl-1,3,8-triaza-spiro[4.5]dec-3-yl]-acetic acid methyl ester | | 451.6 | 452.2 | 10.02 (1) |
| 1h | [8-(2,3-Dihydro-benzo[1,4]dioxin-2-ylmethyl)-4-oxo-1-phenyl-1,3,8-triaza-spiro[4.5]dec-3-yl]-acetic acid methyl ester | | 451.5 | 452.2 | 9.52 (1) |
| 1i | {8-[5-(1,3-Dioxo-1,3-dihydro-isoindol-2-yl)-pentyl]-4-oxo-1-phenyl-1,3,8-triaza-spiro[4.5]dec-3-yl}-acetic acid methyl ester | | 518.6 | 519.2 | 9.68 (1) |
| 1j | (8-Naphthalen-1-ylmethyl-4-oxo-1-phenyl-1,3,8-triaza-spiro[4.5]dec-3-yl)-acetic acid methyl ester | | 443.6 | 444.0 | 9.80 (1) |
| 1k | {8-[2-(4-Fluoro-phenoxy)-ethyl]-4-oxo-1-phenyl-1,3,8-triaza-spiro[4.5]dec-3-yl}-acetic acid methyl ester | | 441.5 | 442.0 | 9.68 (1) |

-continued

| Entry | Name | R²-z-X | MW calculated | LC/MS MH⁺ | rt [min] (method) |
|---|---|---|---|---|---|
| 1l | [8-(6,7-Dimethoxy-2-oxo-2H-chromen-4-ylmethyl)-4-oxo-1-phenyl-1,3,8-triaza-spiro[4.5]dec-3-yl]-acetic acid methyl ester | 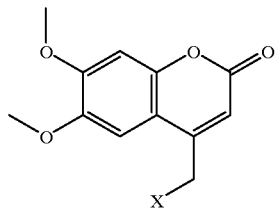 | 521.6 | 522.0 | 8.90 (1) |
| 1m | [8-(2-Naphthalen-1-yl-ethyl)-4-oxo-1-phenyl-1,3,8-triaza-spiro[4.5]dec-3-yl]-acetic acid methyl ester | 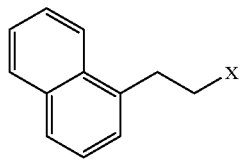 | 457.6 | 458.2 | 10.40 (1) |
| 1n | [8-(3-Cyano-benzyl)-4-oxo-1-phenyl-1,3,8-triaza-spiro[4.5]dec-3-yl]-acetic acid methyl ester | 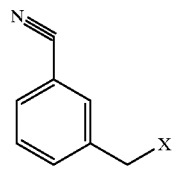 | 418.5 | 419.2 | 9.10 (1) |
| 1o | 3-(3-Methoxycarbonylmethyl-4-oxo-1-phenyl-1,3,8-triaza-spiro[4.5]dec-8-ylmethyl)-benzoic acid methyl ester | 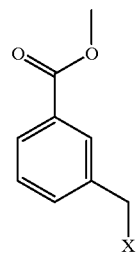 | 451.5 | 452.4 | 9.48 (1) |
| 1p | [8-(4-Bromo-benzyl)-4-oxo-1-phenyl-1,3,8-triaza-spiro[4.5]dec-3-yl]-acetic acid methyl ester | 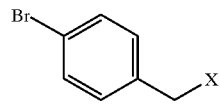 | 472.4 | 472.2 | 10.00 (1) |
| 1q | [8-(3,4-Dichloro-benzyl)-4-oxo-1-phenyl-1,3,8-triaza-spiro[4.5]dec-3-yl]-acetic acid methyl ester | 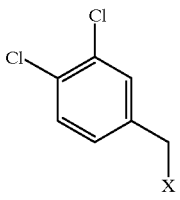 | 462.4 | 462.2 | 10.47 (1) |
| 1r | (8-Anthracen-9-ylmethyl-4-oxo-1-phenyl-1,3,8-triaza-spiro[4.5]dec-3-yl)-acetic acid methyl ester | 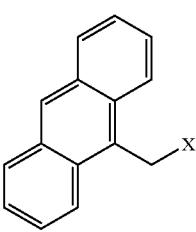 | 493.6 | 494.2 | 11.22 (1) |

Example 2

8-alkylated 4-oxo-1-phenyl-1,3,8-triaza-spiro[4.5]dec-3-yl)-acetic acid methyl esters (Method B)

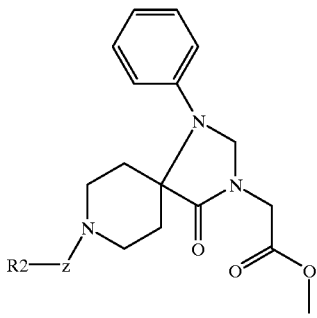

Wang resin with attached 3carboxy-1-phenyl-1,3,8-triazaspiro[4.5]decan-4-one (0.88 mmol/g), prepared similarly as described in example was used for this library of compounds. Equal portions of the resin (62 mg, 0.055 mmol) were placed in Teflon tubes equipped with a frit on a mechanical shaker. The resin was allowed to swell in 2 ml dry tetrahydrofuran for 0.5 h, the solvent was removed with suction and the respective aldehyde (0.275 mmol), dissolved in 1 ml tetrahydrofuran was added, followed by 50% v/v acetic acid (0.225 ml). The mixture was shaken under nitrogen atmosphere at room temperature for 0.5 h. A solution of sodium cyanoborohydride (1 M in tetrahydrofuran, 0.20 ml) was added and the mixture was shaken at room temperature for 16 h. The resin was drained, washed with tetrahydrofuran (2×1 ml), water (2×1 ml), tetrahydrofuran (2×1 ml), dichloromethane (2×1 ml) and tetrahydrofuran/methanol 4:1 (2×1 ml). A solution of sodium methoxide (0.009 mmol) in a mixture of tetrahydrofuran/methanol 4:1 (2 ml) was added to the resin and the suspension was agitated at 50° C. for 16 h. The mixture was neutralized by addition of a solution of acetic acid (0.01 mmol) in a mixture of tetrahydrofuran/methanol 4:1 (1 ml), the solution was drained and the resin was washed with tetrahydrofuran (1 ml). The combined filtrates were concentrated in vacuo to yield the title compounds.

| Entry | Name | R2–Y–CHO | Mw calculated | LC/MS MH+ | rt [min] (method) |
|---|---|---|---|---|---|
| 2a | (8-naphthalen-2-ylmethyl-4-oxo-1-phenyl-1,3,8-triaza-spiro[4.5]dec-3-yl)-acetic acid methyl ester | | 443.6 | 444.2 | 9.93 (1) |
| 2b | [4-oxo-1-phenyl-8-(3-phenyl-allyl)-1,3,8-triaza-spiro[4.5]dec-3-yl]-acetic acid methyl ester | | 419.5 | 420.2 | 9.8 (1) |
| 2c | [8-(4-nitro-benzyl)-4-oxo-1-phenyl-1,3,8-triaza-spiro[4.5]dec-3-yl]-acetic acid methyl ester | | 438.5 | 439.2 | 9.43 (1) |
| 2d | (8-benzofuran-7-ylmethyl-4-oxo-1-phenyl-1,3,8-triaza-spiro[4.5]dec-3-yl)-acetic acid methyl ester | | 433.5 | 434.4 | 9.00 (1) |

-continued

| Entry | Name | R2-Y-CHO | Mw calculated | LC/MS MH+ | rt [min] (method) |
|---|---|---|---|---|---|
| 2e | [8-(2,2-diphenyl-ethyl)-4-oxo-1-phenyl-1,3,8-triaza-spiro[4.5]dec-3-yl]-acetic acid methyl ester | 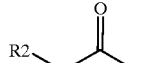 | 483.6 | 484.4 | 8.88 (1) |
| 2f | [8-(2-methoxy-naphthalen-1-ylmethyl)-4-oxo-1-phenyl-1,3,8-triaza-spiro[4.5]dec-3-yl]-acetic acid methyl ester | 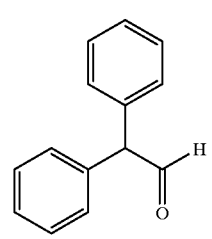 | 473.6 | 474.2 | 9.88 (1) |
| 2g | [8-(4-methoxy-benzyl)-4-oxo-1-phenyl-1,3,8-triaza-spiro[4.5]dec-3-yl]-acetic acid methyl ester | 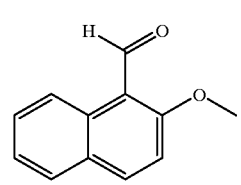 | 423.5 | 424.2 | 8.88 (1) |
| 2h | [4-oxo-1-phenyl-8-(2-phenyl-propyl)-1,3,8-triaza-spiro[4.5]dec-3-yl]-acetic acid methyl ester | 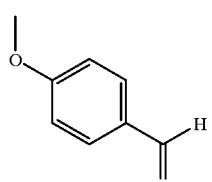 | 421.5 | 422.4 | 9.57 (1) |
| 2i | [8-(5-Bromonaphthalen-1-ylmethyl)-4-oxo-1-phenyl-1,3,8-triazaspiro[4.5]dec-3-yl]-acetic acid methyl ester | 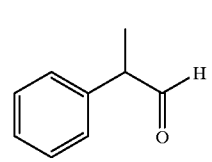 | 522.4 | 522.0 | 10.77 (1) |
| 2j | (8-Indan-5-ymethyl-4-oxo-1-phenyl-1,3,8-triazaspiro[4.5]dec-3-yl(acetic acid methyl ester | 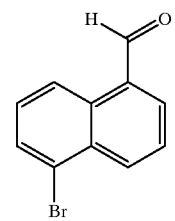 | 433.6 | 434.4 | 10.08 (1) |
| 2k | [8-4-Hydroxybenzyl)-4-oxo-1-phenyl-1,3,8,triazaspirp[4.5]dec-3-yl]acetic acid methyl ester | 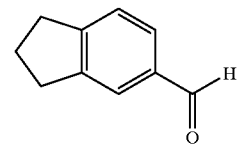 | 409.5 | 410.4 | 8.22 (1) |

-continued

| Entry | Name | R2-Y-CHO | Mw calculated | LC/MS MH+ | rt [min] (method) |
|---|---|---|---|---|---|
| 2l | (8-Furan-2-ylmethyl-4-oxo-1-phenyl=1,3,8-triazaspiro[4.5]dec-3-yl)acetic acid methyl ester | 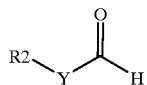 | 383.5 | 384.2 | 8.30 (1) |
| 2m | [8-(4-Dimethylaminobenzyl)-4-oxo-1-phenyl-1,3,8-triazaspiro[4.5]dec-3-yl]acetic acid methyl ester | 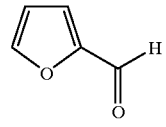 | 436.6 | 437.4 | 7.85 (1) |
| 2n | [8-(3-Bromobenzyl)-4-oxo-1-phenyl-1,3,8-triazaspiro[4.5]dec-3-yl]acetic acid methyl ester | 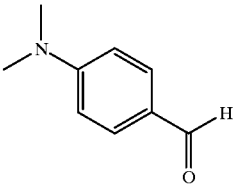 | 472.4 | 472.2 | 9.92 (1) |
| 2o | [8-(2,3-Dimethoxybenzyl)-4-oxo-1-phenyl-1,3,8,triazaspiro[4.5]dec-3-yl]acetic acid methyl ester | 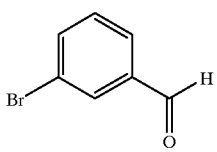 | 453.5 | 454.4 | 9.37 (1) |
| 2p | [8-(2-Bromobenzyl)-4-oxo-1-phenyl-1,3,8-triazaspiro[4.5]dec-3-yl]acetic acid methyl ester | 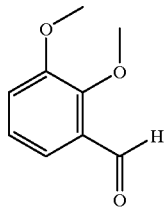 | 472.4 | 474.2 | 9.37 (1) |
| 2q | [8-(5-Ethylfuran-2-ylmethyl)-4-oxo-1-phenyl-1,3,8-triazaspiro[4.5]dec-3-yl]acetic acid methyl ester | 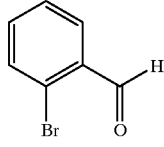 | 411.5 | 412.2 | 9.50 (1) |
| 2r | [8-(4-Methoxynaphthalen-1-ylmethyl)-4-oxo-1-phenyl-1,3,8-triazaspiro[4.5]dec-3-yl]acetic acid methyl ester | 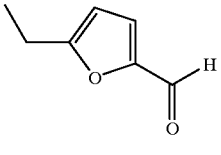 | 473.6 | 474.2 | 10.22 (1) |

-continued

| Entry | Name | R2−Y−CHO | Mw calculated | LC/MS MH+ | rt [min] (method) |
|---|---|---|---|---|---|
| 2s | [8-(3-Methoxy-2-nitrobenzyl)-4-oxo-1-phenyl-1,3,8-triazaspiro[4.5]dec-3-yl]acetic acid methyl ester | 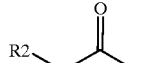 | 468.5 | 469.0 | 9.47 (1) |
| 2t | [8-(5-Methylfuran-2-ylmethyl)-4-oxo-1-phenyl-1,3,8-triazaspiro[4.5]dec-3-yl]acetic acid methyl ester | 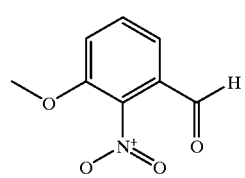 | 397.5 | 398.4 | 9.05 (1) |
| 2u | (8-Benzofuran-2-ylmethyl-4-oxo-1-phenyl-1,3,8-triazaspiro[4.5]dec-3-yl)acetic acid methyl ester | 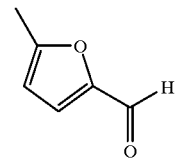 | 433.5 | 434.4 | 9.63 (1) |
| 2v | [8-(2-Iodobenzyl)-4-oxo-1-phenyl-1,3,8-triazaspiro[4.5]dec-3-yl]acetic acid methyl ester | 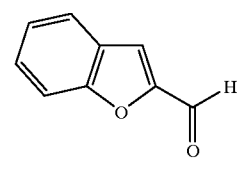 | 519.4 | 520.2 | 9.65 (1) |
| 2w | [8-(4-Methoxy-2,3-dimethylbenzyl)-4-oxo-1-phenyl-1,3,8-triazaspiro[4.5]dec-3yl]acetic acid methyl ester | 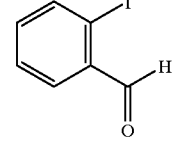 | 451.6 | 452.4 | 9.50 (1) |
| 2x | [8-(4-Dimethylaminonaphthalen-1-ylmethyl)-4-oxo-1-phenyl-1,3,8-triazaspiro[4.5]dec-3-yl]acetic acid methyl ester | 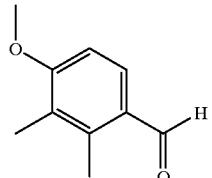 | 486.6 | 487.4 | 8.62 (1) |
| 2y | [8-(2,3,4-trimethoxybenzyl)-4-oxo-1-phenyl-1,3,8-triazaspiro[4.5]dec-3-yl]acetic acid methyl ester | 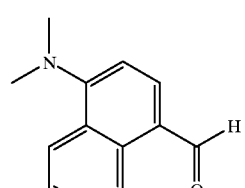 | 483.6 | 484.4 | 9.20 (1) |

| Entry | Name | R2–Y–CHO | Mw calculated | LC/MS MH+ | rt [min] (method) |
|---|---|---|---|---|---|
| 2z | [8-(1-Methyl-1H-indol-3-ylmethyl)-4-oxo-1-phenyl-1,3,8-triazaspiro[4.5]dec-3-yl]acetic acid methyl ester | 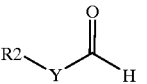 | 446.6 | 447.2 | 9.28 (1) |
| 2aa | [8-(2,4-Diethoxy-3-methylbenzyl)-4-oxo-1-phenyl-1,3,8-triazaspiro[4.5]dec-3-yl]acetic acid methyl ester | 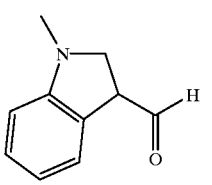 | 495.6 | 496.2 | 11.00 (1) |

Example 3

2-(8-naphthalen-1-ylmethyl-4-oxo-1-phenyl-1,3,8-triaza-spiro[4.5]dec-3-yl)-propionic acid ethyl ester hydrochloride

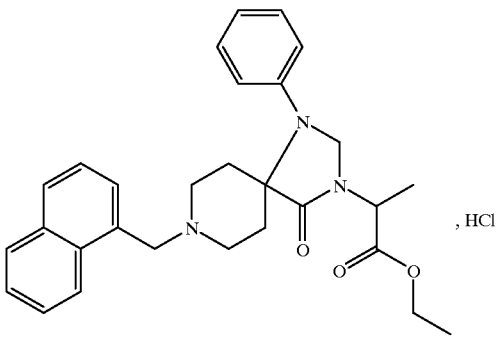

Sodium hydride, 60% (0.156 g, 3.9 mmol) was suspended in dry heptane (5 ml) and stirred under nitrogen for 5 minutes. The solvent was decanted and dry dimethyl formamide (2 ml) was added. 8Naphthalen-1-ylmethyl-1-phenyl-1,3,8-triazaspiro[4.5]decan-4-one (1.115 g, 3.0 mmol), dissolved in dry dimethyl formamide (11 ml) was added dropwise under cooling in an ice bath. The mixture was stirred at 0° C. for 1 h. An aliquot of the resulting solution of deprotonated 1-phenyl-8-naphthalen-1-ylmethyl-1,3,8-triazaspiro[4.5]decan-4-one (2.3 ml, 0.5 mmol) was added to ethyl 2-bromopropionate and the mixture was stirred at room temperature overnight. Water (15 ml) and ethyl acetate (15 ml) were added and the mixture was shaken, the organic phase was separated and successively washed with water (2×10 ml) and brine (10 ml). The organic phase was dried over magnesium sulfate and the solvent was evaporated in vacuo. The crude product was purified by column chromatography on silica gel using a mixture of ethyl acetate and dichloromethane 1:4 to give the pure base, which was dissolved in tetrahydrofuran (3 ml) and an excess of a solution of hydrogen chloride in ether was added. Crystallization occurred on the careful addition of ether (6 ml). The precipitate was collected by filtration and dried to give the title compound (217 mg, 85% yield).

M.p. 175–181° C.

Calculated for $C_{29}H_{33}N_3O_3$, HCl: C, 68.56%; H, 6.75%; N, 8.27%; Found: C, 68.36%; H, 7.03%; N, 7.93%.

Following the same preparation method, the following compounds were prepared:

3-Methyl-2-(8-naphthalen-1-ylmethyl-4-oxo1-phenyl-1,3,8-triaza-spiro[4.5]dec-3-yl)-butyric acid ethylester hydrochloride

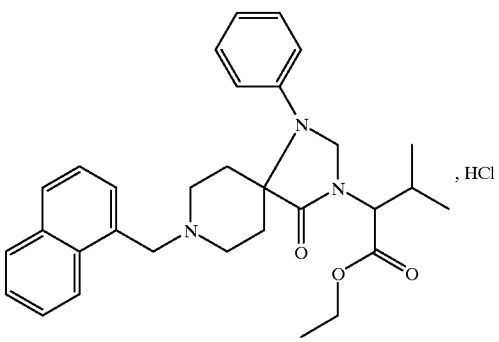

LC/MS (Method 2): m/e=500.2 (MH+); RT=6.60 min.

Calculated for $C_{31}H_{37}N_3O_3$, HCl, 0.25 $H_2O$: C, 69.45%; H, 7.14%; N, 7.84%; Found: C, 68.87%; H, 7.18%; N, 7.77%.

31

2-(8-Naphthalen-1-ylmethyl-4-oxo-1-pheny-1,3,8-triaza-spiro[4.5]dec-3-yl)-hexanoic acid ethyl ester hydrochloride

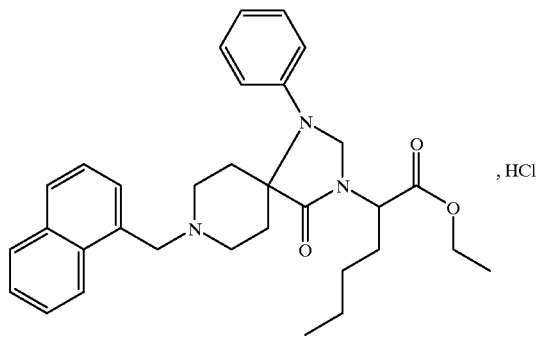

M.p. 169–177 °C.

Calculated for $C_{32}H_{39}N_3O_3$, HCl, 0.75 $H_2O$: C, 68.19%; H, 7.42%; N, 7.45%; Found: C, 67.92%; H, 7.47%; N, 7.34%.

5-(8-Naphthalen-1-ylmethyl-4-oxo-1-phenyl-1,3,8-triaza-spiro[4.5]dec-3-yl)-pentaoic acid ethyl ester hydrochloride

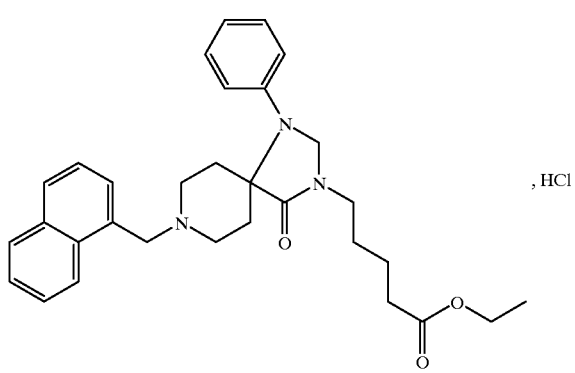

LC/MS (Method 2): m/e=500.2 (MH+); RT=6.08 min.

Calculated for $C_{31}H_{37}N_3O_3$, HCl, 1.25 $H_2O$: C, 66.12%; H, 7.34%; N, 7.46%; Found: C, 66.23%; H, 7.13%; N, 7.34%.

32

4-(8-Naphthalen-1-ylmethyl-4-oxo-1-phenyl-1,3,8-triaza-spiro[4.5]dec-3-yl)-butyric acid ethyl ester hydrochloride

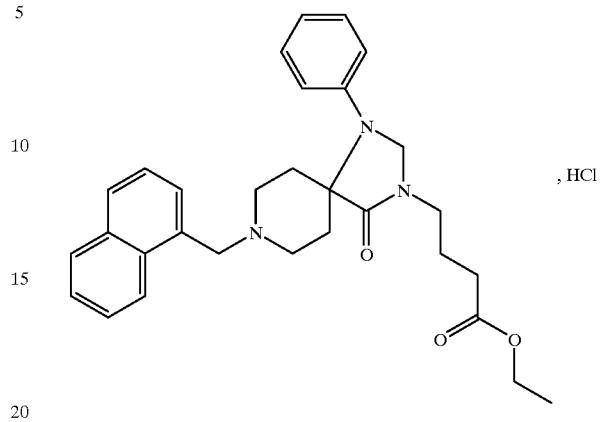

M.p. 200–203° C.

Calculated for $C_{30}H_{35}N_3O_3$ HCl, 0.3 tetrahydrofuran: C, 68.92%; H, 7.12%; N, 7.73%; Found: C, 68.63%; H, 7.08%; N, 7.64%.

Example 4

8-Naphthalen-1-ylmethyl-1-phenyl-1,3,8-triaza-spiro[4.5]decan-4-one

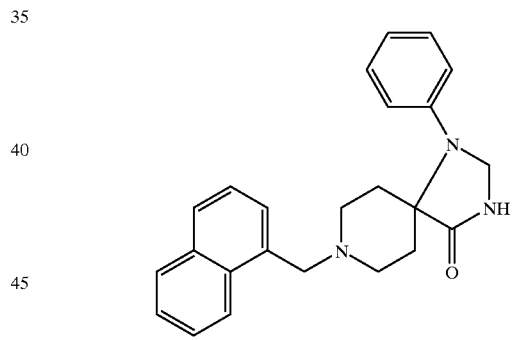

1-Phenyl-1,3,8-triaza-spiro[4.5]decan-4-one (185.04 g, 0.76 mol) was suspended in 2-butanone (3600 ml). 1-(Chloromethyl)naphthalene (169.21 g, 0.91 mol), dry potassium carbonate (345.42 g, 2.50 mol) and sodium iodide (113.91 g, 0.76 mol) were added and the mixture was heated at reflux temperature for 24 h. The solvent was evaporated in vacuo and the remainder was distributed between water (2000 ml) and diethyl ether (2000 ml). The formed precipitate was collected by filtration, washed successively with water (800 ml), toluene (600 ml) and ice cold acetone (2×200 ml) and dried affording the title compound as a powder (191.20 g, 68% yield).

M.p. 207–215 °C.

Calculated for $C_{24}H_{25}N_3O$: C, 77.60%; H, 6.78%; N, 11.31%; Found: C, 77.23%; H, 6.90%; N, 11.29%.

Example 5

(8-Naphthalen-1-ylmethyl-4-oxo1-phenyl-1,3,8-triaza-spiro[4.5]dec-3-yl)-acetic acid methyl ester

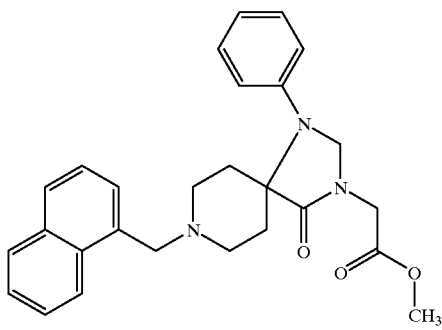

Sodium hydride (60%, 12.96 g, 0.324 mol) was stirred with dry n-heptane under nitrogen and the solvent was decanted from the settled hydride. Ice cold dimethyl formamide (600 ml) was added and the resulting solution was added during 0.5 h to a stirred solution of 8-naphthalen-1-ylmethyl-1-phenyl-1,3,8-triaza-spiro[4.5]decan-4-one (prepared as described in example 4) in dimethyl formamide (900 ml) at 0–5° C. After stirring for additional 0.5 h, a solution of methyl bromoacetate (54.84 g, 0.348 mol) in dimethylformamide (20 ml) was added under ice cooling. The reaction mixture was allowed to warm up to room temperature while stirring for additional 1 h and was then poured into a mixture of ethyl acetate (800 ml) and ice water (1900 ml) under vigorous stirring. The organic phase was separated and the aqueous phase was extracted with ethyl acetate (2×400 ml). The combined organic phases were successively washed with water (2×300 ml) and brine (2×250 ml) and dried over magnesium sulfate. The solution was concentrated in vacuo, ethyl acetate (30 ml) was added to the warm residue under stirring and crystallization was completed by cooling to room temperature. The product was filtered, washed on the filter with ice cold ethyl acetate and dried, to afford the title compound (111.06 g, 83% yield) as a powder.

M.p. 122–135° C.

Calculated for $C_{27}H_{29}N_3O_3$: C, 73.11%; H, 6.59%; N, 9.47%; Found: C, 72.84%; H, 6.71%; N, 9.36%.

Example 6

(8-Naphthalen-1-ylmethyl-4-oxo-1-phenyl-1,3,8-triaza-spiro[4.5]dec-3-yl)-acetic acid

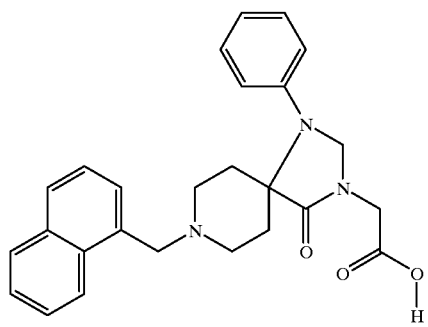

(8-Naphthalen-1-ylmethyl-4-oxo-1-phenyl-1,3,8-triaza-spiro[4.5]dec-3-yl)-acetic acid methyl ester (44.40 g, 0.1 mol, prepared as described above) was dissolved in a mixture of 2 N sodium hydroxide (165 ml, 0.33 mol) and ethanol (500 ml) and stirred at room temperature for 16 h. Dichloromethane (700 ml) was added and pH was adjusted to 5 by the addition of 6 N hydrochloric acid. The organic phase was separated, washed with water (2×200 ml and concentrated to 300 ml in vacuo. Water (300 ml) and dichloromethane (100 ml) were added and the slurry was stirred overnight. The product was collected by filtration, washed successively with water (4×100 ml, dichloromethane (2×50 ml) and acetone (2×50 ml) and dried, affording the title compound as a powder (44.6 g, 97% yield).

$^1$H NMR (200 MHz, DMSO-$d_6$) δ1.62 (d, 2H), 2.56 (q, 2H), 2.88 (m, 4H), 4.03 (s, 2H), 4.07 (s, 2H), 4.68 (s, 2H), 6.78 (t, 1 H), 6.84 (d, 2H), 7.23 (d, 2H), 7.40–7.70 (m, 4H), 7.90 (dd, 2H), 8.42 (d, 1H).

Calculated for $C_{26}H_{27}N_3O_3$, 1.25 $H_2O$: C, 69.08%; H, 6.58%; N, 9.30%; Found: C, 68.89%; H, 6.39%; N, 9.13%.

Example 7

(8-Naphthalen-1-ylmethyl-4-oxo-1-phenyl-1.3,8-triaza-spiro[4.5]dec-3-yl)-acetylglycine methyl ester

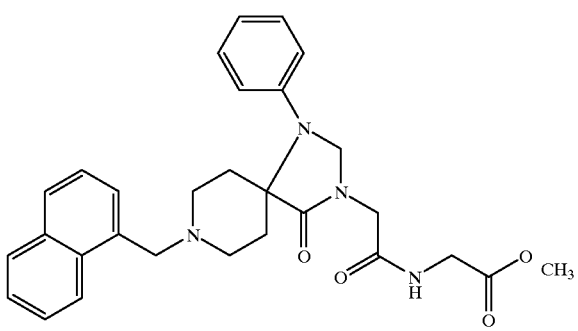

Wang resin loaded with Fmoc-glycine (88 mg, 0.045 mmol) was placed in a Teflon tube equipped with a frit on a mechanical shaker. The resin was allowed to swell in dimethyl formamide (1.5 ml) for 1 h. The solvent was removed by suction and the resin was agitated with 20% piperidine in N,N-dimethylformamide (1.5 ml) for 30 minutes. The solution was removed by suction and the resin was washed with N,N-dimethylformamide (3×1.5 ml). To a solution of (8-naphthalen-1-ylmethyl-4-oxo-1-phenyl-1,3,8-triaza-spiro[4.5]dec-3-yl)-acetic acid (0.0773 g, 0.18 mmol) in dimethyl formamide (1.6 ml), diisopropylcarbodiimide (29 μl, 0.18 mmol) and 1-hydroxy-1H-benzotriazol (0.0243 g, 0.18 mmol) were added and the mixture was stirred at room temperature for 0.5 h. The resulting solution and diisopropylethylamine (31 μl, 0.18 mmol) were added to the above resin and this was shaken at room temperature overnight. The resin was filtered and washed with dimethylformamide (2×1.5 ml), dichloromethane (4×1.5 ml), methanol (2×1.5 ml) and tetrahydrofuran/methanol 4:1 (2×1.5 ml). A solution of sodium methoxide (0.009 mmol) in a mixture of tetrahydrofuran/methanol 4:1 (2 ml) was added to the resin and the suspension was agitated at 50 ° C. for 16 h. The mixture was neutralized by addition of a solution of acetic acid (0.01 mmol) in a mixture of tetrahydrofuran/methanol 4:1 (1 ml), the solution was drained and the resin was washed with tetrahydrofuran (1 ml). The combined filtrates were concentrated in vacuo to afford the title compound.

The following compounds were parallel synthesized using the above described method:

| Entry | Name | Amino acid-resin | Mw calculated | LC/MS MH+ | rt[min] (method) |
|---|---|---|---|---|---|
| 7a | [2-(8-Naphthalen-1-ylmethyl-4-oxo-1-phenyl-1,3,8-triaza-spiro[4.5]dec-3-yl)-acetylamino]-acetic acid methyl ester | Fmoc-Gly-Wang | 500.6 | 501.4 | 9.58 (1) |
| 7b | 2-(S)-[2-(8-Naphthalen-1-ylmethyl-4-oxo-1-phenyl-1,3,8-triaza-spiro[4.5]dec-3-yl)-acetylamino]-propionic acid methyl ester | Fmoc-Ala-Wang | 514.2 | 515.4 | 9.80 (1) |
| 7c | 3-Methyl-2-(S)-[2-(8-naphthalen-1-ylmethyl-4-oxo-1-phenyl-1,3,8-triaza-spiro[4.5]dec-3-yl)-acetylamino]-pentanoic acid methyl ester | Fmoc-Ile-Wang | 556.7 | 557.4 | 11.33 (1) |
| 7d | 4-Methyl-2-(S)-[2-(8-naphthalen-1-ylmethyl-4-oxo-1-phenyl-1,3,8-triaza-spiro[4.5]dec-3-yl)-acetylamino]-pentanoic acid methyl ester | Fmoc-Leu-Wang | 556.7 | 557.4 | 11.58 (1) |
| 7e | 4-Methylsulfanyl-2-(S)-[2-(8-naphthalen-1-ylmethyl-4-oxo-1-phenyl-1,3,8-triaza-spiro[4.5]dec-3-yl)-acetylamino]-butyric acid methyl ester | Fmoc-Met-Wang | 574.7 | 575.2 | 10.53 (1) |
| 7f | 2-(S)-[2-(8-Naphthalen-1-ylmethyl-4-oxo-1-phenyl-1,3,8-triaza-spiro[4.5]dec-3-yl)-acetylamino]-3-phenyl-propionic acid methyl ester | -Fmoc-Phe Wang | 590.7 | 591.4 | 11.57 (1) |
| 7g | 3-(1H-Indol-3-yl)-2-(S)-[2-(8-naphthalen-1-ylmethyl-4-oxo-1-phenyl-1,3,8-triaza-spiro[4.5]dec-3-yl)-acetylamino]-propionic acid methyl ester | Fmoc-Trp(Boc)-Wang | 629.8 | 630.4 | 10.43 (1) |
| 7h | 3-Methyl-2-(S)-[2-(8-naphthalen-1-ylmethyl-4-oxo-1-phenyl-1,3,8-triaza-spiro[4.5]dec-3-yl)-acetylamino]-butyric acid methyl ester | Fmoc-Val-Wang | 542.7 | 543.2 | 10.57 (1) |
| 7i | 5-Guanidino-2-(S)-[2-(8-naphthalen-1-ylmethyl-4-oxo-1-phenyl-1,3,8-triazaspiro-[4.5]dec-3-yl)-acetylamino]-pentanoic acid methylester | Fmoc-Arg(Pbf)-Wang | 599.7 | 600.2 | 8.23 (1) |

Example 8

5-Guanidino-(S)-2-[2-(8-naphthalen-1-ylmethyl-7-oxo-1,3,8-triaza-spiro[4.5]dec-3-yl)-acetylamino]-pentanoic acid amide, ditrifluoroacetate

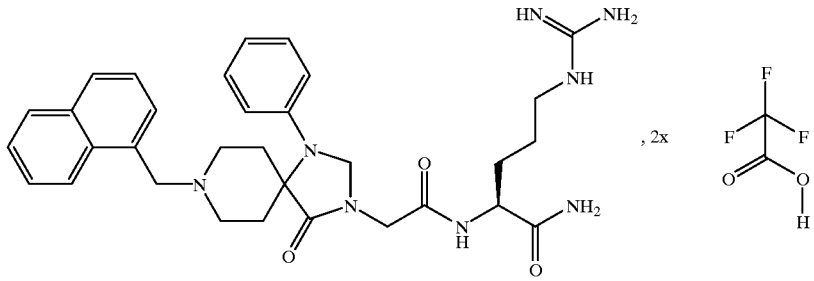

One equivalent (1.0 g, 0.69 mmol) of Rink Amide (AM) resin (0.69 mmol/g, purchased from Novabiochem) was suspended in piperidine/N,N-dimethylformamide (20%) (all volumes are calculated as 10 ml/gram of resin) and shaken on a mechanical shaking apparatus for 0.5 h. The resin was filtered, rinsed with N,N-dimethylformamide, suspended in piperidine/N,N-dimethyiformamide (20%) and shaken for 0.5 h. The resin was filtered and washed as follows: 3×N,N-dimethylformamide/water (90%), 2×ethanol, 3×N,N-dimethylformamide, 5×methylene chloride. The resin was dried in vacuo and suspended in N,N-dimethylformamide. Fmoc-Arg(Pbf).OH (1.7 g, 01.7 mmol, 4 equivalents), EDAC (N-(3-dimethylaminopropyl)-N'-ethyl carbodiimide hydrochloride) (0.51 g, 2.68 mmol, 4 equivalents), and HOBT (1-hydroxybenzotriazole) (0.36 g, 2.68 mmol, 4 equivalents) were added and the reaction was allowed to shake for 16 h. The resin was filtered and washed successively with 3×N,N-dimethylformamide/water (90%), 3×N,N-dimethylformamide, 3×methylene chloride, was suspended in piperidine/N,N-dimethylformamide (20%) and shaken for 0.5 h. The resin was filtered and washed as follows: 3×N,N-dimethylformamide/water (90%), 2×ethanol, 3×N,N-dimethylformamide, 5×methylene chloride. The resin was dried in vacuo and suspended in N,N-dimethylformamide and (8-naphthalen-1-ylmethyl-4-oxo-1-phenyl-1,3,8-triaza-spiro[4.5]dec-3-yl)-acetic acid (1.08 g, 2.51 mmol, 3.6 equivalents) was added followed by EDAC (0.47 g, 2.51 mmol, 3.6 equivalents), HOBT (0.33 g, 2.51 mmol, 3.6 equivalents) and the reaction was allowed to stir at room temperature for 20 h. The resin was filtered and washed 3×N,N-dimethylformamide/water (90%), 3×N,N-dimethylformamide, 3 ×methylene chloride and dried in vacuo. The resin was suspended in trifluoroacetic acid/water (95%) and shaken for 2 h. The filtrate was collected and added dropwise to cyclohexane/ether (50%) after which a white precipitate was observed. This white solid was collected and washed 3×cyclohexane/ether (50%) with the aid of a centrifuge. This was dissolved in a minimum amount of acetonitrile/water (10%) and lyophilized affording the title compound (273 mg, 50% yield), as a white powder.

HPLC retention time=11.01 minutes (5 μm C184×250 mm column, eluting with a 20–80% gradient of 0.1% trifluoroacetic acid/acetonitrile and 0.1% trifluoroacetic acid/water over 30 minutes at 35° C.).

LC/MS (Method 2): m/e 585.4 ((MH+); RT=4.43 min.

5-Guanidino-(R)-2-[-(8-naphthalen-1-ylmethyl-7-oxo-1.3.8-triaza-spiro[4.5]dec-3-yl)-acetylamino]-pentanoic acid amide, di-trifluoroacetate This compound was prepared and purified analogously to EXAMPLE 8 using Rink Amide (AM) Resin (0.69 mmol/g) (0.200 g, 0.138 mmol, 1 equivalent), Fmoc-.D-Arg(Pbf).OH (0.358 g, 0.552 mmol, 4 equivalents) to yield the title compound (73 mg, 59% yield) as a white powder. This powder was assumed to be salted with two equivalents of trifluoroacetic acid.

LC/MS (Method 2): m/e=585.2 (MH+); RT=4.42 min.

$^1$H NMR (400 MHz, DMSO-$d_6$) δ1.4 (bm, 3H), 1.7 (bm, 1H), 1.8–1.9 (bm, 2H), 2.8 (bm, 2H), 3.1 (m, 2H), 3.4–3.5 (bm, 4H), 3.7 (bm, 1H), 4.1 (s, 2H), 4.2 (m, 1H), 4.6 (m, 2H), 4.84.9 (bm, 1H), 6.6–7.4 (bm, 4H), 6.7 (m, 1H), 6.9 (m, 2H), 7.1 (s, 1H), 7.2 (t, J=9 Hz, 2H), 7.4 (s, 1H), 7.0–7.2 (m, 4H), 7.9 (bs, 1H), 8.0 (m, 2H), 8.4 (t, J=9 Hz, 2H), 10.2 (bs, 1H).

$^{13}$C NMR (75 MHZ, DMSO-$d_6$) δ24.62, 25.94, 28.61, 42.37, 48.19, 51.63, 57.22, 63.14, 114.17, 118.02, 123.53, 124.84, 125.77, 126.57, 128.31, 128.70, 131.64, 132.97, 141.91, 156.23, 166.06, 172.62, 6 carbons obscured.

Example 9A

N-Benzyl-2-(8-naphthalen-1-ylmethyl-4-oxo-1-phenyl-1,3,8-triaza-spiro[4.5]dec-3-yl)-acetamide

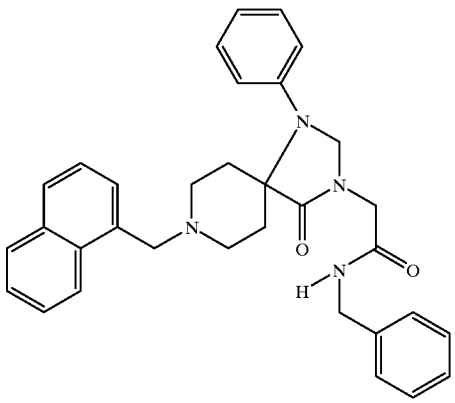

To a suspension of the the commercially available aminomethylated polystyrene resin (Novabiochem) (20 g, 16 mmol) in dimethylformamide (70 ml) was added a solution of the commercially available BAL-Linker (PerSeptive Biosystems GMBH) (12.88 g, 48.0 mmol) and 1-hydroxybenzotriazole (7.26 g, 48.0 mmol) in 70 ml of dimethylformamide. To this was added N,N'- diisopropylcarbodiimide (6.06 g, 48.0 mmol) followed by N,N-diisopropylethylamine (6.19 g, 48.0 mmol). The reaction was allowed to stir 20 h at room temperature. The resin was filtered and washed as follows: 3×dimethylformamide (50 ml), 3×tetrahydrofuran (50 ml), 3×dichloromethane (50 ml), 3×ether (50 ml). The resin was dried in vacuo and isolated: 23.92 g. IR spectroscopy showed an aldehyde stretching band at 1674 cm$^{-1}$. To a part of this resin (0.200 g, 0.160 mmol) in 1,2-dichloroethane (8 ml) at room temperature, was added benzyl amine (0.171 g, 1.60 mmol) followed by sodium triacetoxyborohydride (0.339 g, 1.60 mmol). The reaction was allowed to shake 20 h at room temperature, filtered and washed as follows: 3×dimethylformamide/water (90/10) (8 ml); 3×dimethylformamide (8 ml); 3×dichloromethane (8 ml). The resin was suspended in dimethylformamide, treated with (8-naphthalen-1-ylmethyl-4-oxo-1-phenyl-1,3,8-triaza-spiro[4.5]dec-3-yl)-acetic acid (0.274 g, 0.640 mmol), 1-hydroxybenzotrazole (0.099 9, 0.640 mmol) and N,N'-diisopropylcarbodiimide (0.081 g, 0.640 mmol). The reaction was allowed to shake for 20 h at room temperature. The resin was filtered, suspended in dimethylsulfoxide and heated to 40° C. for 1 h. The resin was again filtered, suspended in dimethylsulfoxide (8 ml) and heated to 40° C. for 1 h. The resin was filtered and washed as follows: 3×dimethylformamide/water (90/10) (8 ml); 3×dimethylformamide (8 ml); 3×dichloromethane (8 ml) and air-dried. The resin was treated with trifluoroacetic acid/water (95/5) (8 ml) for 1 h at room temperature. The filtrate was collected and concentrated in vacuo to give the desired product.

The above example and the following compounds were synthesized in a parallel fashion using the above procedure and the appropriate amine.

| Entry | Name | Amine | MW calculated | LCMS MH+ | rt(min) (method) |
|---|---|---|---|---|---|
| 9a | N-benzyl-2-(8-naphthalen-1-ylmethyl-4-oxo-1-phenyl-1,3,8-triaza-spiro[4.5]dec-3-yl)-acetamide | benzylamine | 518 | 519 | 5.34 (2) |
| 9b | N-phenethyl-2-(8-naphthalen-1-ylmethyl-4-oxo-1-phenyl-1,3,8-triaza-spiro[4.5]dec-3-yl)-acetamide | phenethylamine | 532 | 533 | 5.40 (2) |
| 9c | N-(N-3-propylmorphoino)-2-(8-naphthalen-1-ylmethyl-4-oxo-1-phenyl-1,3,8-triaza-spiro[4.5]dec-3-yl)-acetamide | N-(3-aminopropyl)-morpholine | 555 | 556 | 4.27 (2) |
| 9d | N-hexyl-2-(8-naphthalen-1-ylmethyl-4-oxo-1-phenyl-1,3,8-triaza-spiro[4.5]dec-3-yl)-acetamide | N-hexylamine | 512 | 513 | 5.90 (2) |
| 9e | N-furfuryl-2-(8-naphthalen-1-ylmethyl-4-oxo-1-phenyl-1,3,8-triaza-spiro[4.5]dec-3-yl)-acetamide | furfurylamine | 508 | 509 | 5.10 (2) |
| 9f | N-(3-phenyl-1-propyl)-2-(8-naphthalen-1-ylmethyl-4-oxo-1-phenyl-1,3,8-triaza-spiro[4.5]dec-3-yl)-acetamide | 3-phenyl-1-propyl-amine | 546 | 547 | 5.60 (2) |
| 9g | N-(2-methoxyethyl)-2-(8-naphthalen-1-ylmethyl-4-oxo-1-phenyl-1,3,8-triaza-spiro[4.5]dec-3-yl)-acetamide | 2-methoxyethyl-amine | 486 | 487 | 4.67 (2) |

-continued

| Entry | Name | Amine | MW calculated | LCMS MH+ | rt(min) (method) |
|---|---|---|---|---|---|
| 9h | N-(cyclohexanemethyl)-2-(8-naphthalen-1-ylmethyl-4-oxo-1-phenyl-1,3,8-triaza-spiro[4.5]dec-3-yl)-acetamide | cycohexane-methylamine | 524 | 525 | 6.04 (2) |
| 9i | N-(4-methoxybenzyl)-2-(8-naphthalen-1-ylmethyl-4-oxo-1-phenyl-1,3,8-triaza-spiro[4.5]dec-3-yl)-acetamide | 4-methoxybenzyl-amine | 548 | 549 | 5.34 (2) |
| 9j | N-pipieronyl-2-(8-naphthalen-1-ylmethyl-4-oxo-1-phenyl-1,3,8-triaza-spiro[4.5]dec-3-yl)-acetamide | piperonylamine | 562 | 563 | 5.30 (2) |
| 9k | N-(tetrahydrofurfuryl)-2-(8-naphthalen-1-ylmethyl-4-oxo-1-phenyl-1,3,8-triaza-spiro[4.5]dec-3-yl)-acetamide | tetrahydrofurfuryl-amine | 512 | 513 | 4.74 (2) |
| 9l | N-(2-methoxyphenyl)-2-(8-naphthalen-1-ylmethyl-4-oxo-1-phenyl-1,3,8-triaza-spiro[4.5]dec-3-yl)-acetamide | 2-methoxyphen-ethylamine | 562 | 563 | 5.64 (2) |
| 9m | N-(4-phenylbutyl)-2-(8-naphthalen-1-ylmethyl-4-oxo-1-phenyl-1,3,8-triaza-spiro[4.5]dec-3-yl)-acetamide | 4-phenylbutyl-amine | 560 | 561 | 6.17 (2) |
| 9n | N-[4-(2-aminoethyl-pyridine)]-2-(8-naphthalen-1-ylmethyl-4-oxo-1-phenyl-1,3,8-triaza-spiro[4.5]dec-3-yl)-acetamide | 4-(2-aminoethyl)-pyridine | 533 | 534 | 4.40 (2) |
| 9o | N-(4-methoxyphenethyl)-2-(8-naphthalen-1-ylmethyl-4-oxo-1-phenyl-1,3,8-triaza-spiro[4.5]dec-3-yl)-acetamide | 4-methoxyphen-ethylamine | 562 | 563 | 5.30 (2) |
| 9p | N-[1-(3-aminopropyl)-2-pyrrolidnonyl]-2-(8-naphthalen-1-ylmethyl-4-oxo-1-phenyl-1,3,8-triaza-spiro[4.5]dec-3-yl)-acetamide | 1-(3-aminopropyl)-2-pyrrolidinone | 553 | 554 | 4.70 (2) |
| 9q | N-napthylenemethyl-2-(8-naphthalen-1-ylmethyl-4-oxo-1-phenyl-1,3,8-triaza-spiro[4.5)dec-3-yl)-acetamide | 1-napthalene-methylamine | 568 | 569 | 6.17 (2) |
| 9r | N-[4-(tert-butyl)benzyl]-2-(8-naphthalen-1-ylmethyl-4-oxo-1-phenyl-1,3,8-triaza-spiro[4.5]dec-3-yl)-acetamide | 4-(tert-butyl)benzylamine | 574 | 575 | 6.51 (2) |
| 9s | N-(2-phenoxyethyl)-2-(8-naphthalen-1-ylmethyl-4-oxo-1-phenyl-1,3,8-triazaspiro[4.5]dec-3-yl)-acetamide | 2-phenoxy-ethylamine | 548 | 549 | 5.37 (2) |

Example 10A 2-(S)-[2-(8-Naphthalen-1-ylmethyl-4-oxo1-phenyl-1,3,8-triaza-spiro[4.5]dec-3-yl)-acetylamino]-5ureido-pentanoic acid amide

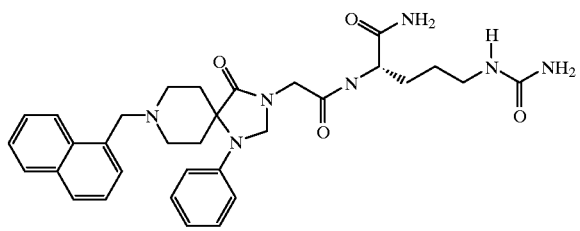

Rink Amide (AM) resin (Novabiochem) (0.200 g, 0.138 mmol) was suspended in dimethylformamide/piperidine (80/20) (8 ml) and shaken for 30 min at room temperature. The resin was filtered and rinsed with dimethylformamide (8 ml) and again suspended in dimethylformamide/piperidine (80/20) (8 ml) and shaken for 30 min at room temperature; the resin was washed as follows: 3×dimethylformamide/water (90/10) (8 ml), 3×dimethylformamide (8 ml), 3×dichloromethane (8 ml). The resin was suspended in dimethylformamide (8 ml), Fmoc-L-2-amino-5-ureido-n-valeric acid (L-Fmoc-Cit-OH) (0.227 g, 0.552 mmol) and 1-hydroxybenzotriazole (0.085 g, 0.552 mmol) were added. N,N'-diisopropylcarbodiimide (0.071 g, 0.552 mmol) was added and the reaction was allowed to shake for 20 h at room temperature. The resin was filtered and washed as follows: 3×dimethylformamide/water (90/10) (8 ml), 3×dimethylformamide (8 ml), 3×dichloromethane (8 ml). The resin was suspended in dimethylformamide/piperidine (80/20) (8 ml) and shaken for 30 min at room temperature. The resin was filtered and rinsed with dimethylformamide (8 ml) and again suspended in dimethylformamide/piperidine (80/20) (8 ml) and shaken for 30 min at room temperature; the resin was washed as follows: 3×dimethylformamide/water (90/10) (8 ml), 3×dimethylformamide (8 ml), 3×dichloromethane (8 ml). The resin was suspended in dimethylformamide (8 ml); (8-naphthalen-1-ylmethyl-4-oxo-1-phenyl-1,3,8-triaza-spiro[4.5]dec-3-yl)-acetic acid (0.269 g, 0.552 mmol), 1-hydroxybenzotriazole (0.085 g, 0.552 mmol) and N,N'-diisopropylcarbodiimide (0.071 g, 0.552 mmol) were added. The reaction mixture was allowed to shake at room temperature for 20 h and filtered. The resin was suspended in dimethylsulfoxide (8 ml) and heated to 40° C. for 1 h. The resin was again filtered, suspended in dimethylsulfoxide (8 ml) and heated to 40° C. for an additional 1 h. The resin was filtered and washed as follows: 3×dimethylformamide/water (90/10) (8 ml); 3×dimethylformamide (8 ml); 3×dichloromethane (8 ml) and air-dried. The resin was treated with trifluroacetic acid/water (95/5) (8 ml) for 2 h at room temperature. The filtrate was collected and concentrated in vacuo to give the desired product.

The above example and the following examples were synthesized in a parallel manner using the procedure outlined above with the appropriate L-Fmoc-protected amino acid. For examples 10b and 10c, the TFA/water cleavage filtrate was added dropwise into a solution of heptane/ether (50/50) (10 ml) at 0° C. Compound 10b precipitated and was collected as a white solid. For example 10c, an oily residue was formed, the heptane/ether solution was decanted, the residue was taken up into water/acetonitrile (90/10) (10 ml) and freeze-dried to give a white powder.

| Entry | Name | L-Amino Acid | MW calculated | LCMS MH+ rt(min) (method) |
|---|---|---|---|---|
| 10a | 2-(S)-[2-(8-Naphthalen-1-ylmethyl-4-oxo-1-phenyl-1,3,8-triaza-spiro[4.5]dec-3-yl)-acetylamino]-5-ureido-pentanoic acid amide | Fmoc-Cit-OH | 472 | 586 4.40 (2) |
| 10b | 2-(S)-[2-(8-Naphthalen-1-ylmethyl-4-oxo-1-phenyl-1,3,8-triaza-spiro[4.5]dec-3-yl)-acetylamino]-pentanedioic acid diamide | Fmoc-Gln(trt)-OH | 556 | 557 4.47 (2) |
| 10c | 3-[(1H-Imidazol-4-yl)-2-(S)-[2-(8-naphthalen-1-ylmethyl-4-oxo-1-phenyl-1,3,8-triaza-spiro[4.5]dec-3-yl)-acetylamino]-propionamide | Fmo-His(trt)-OH | 565 | 566 4.14 (2) |
| 10d | 6-[Amino-2-(S)-[2-(8-naphthalen-1-ylmethyl-4-oxo-1-phenyl-1,3,8-triaza-spiro[4.5]dec-3-yl)-acetylamino]-hexanoic acid amide | Fmoc-Lys(Boc)-OH | 556 | 557 4.27 (2) |
| 10e | 1-[2-(8-Naphthalen-1-ylmethyl-4-oxo-1-phenyl-1,3,8-triaza-spiro[4.5]dec-3-yl)-acetyl]-pyrrolidine-2-(S)-carboxylic acid amide | Fmoc-Pro-OH | 525 | 526 4.64 (2) |
| 10f | 3-Hydroxy-2-(S)-[2-(8-naphthalen-1-ylmethyl-4- | Fmoc-Ser(t-Bu)-OH | 515 | 516 4.50 (2) |

-continued

| Entry | Name | L-Amino Acid | MW calculated | LCMS MH+ | rt(min) (method) |
|---|---|---|---|---|---|
| | oxo-1-phenyl-1,3,8-triaza-spiro[4.5]dec-3-yl)-acetylamino]-propionamide | | | | |
| 10h | 3-(1H-Indol-3-yl)-2-(S)-[2-(8-naphthalen-1-ylmethyl-4-oxo-1-phenyl-1,3,8-triaza-spiro[4.5]dec-3-yl)-acetylamino]-propionamide | Fmoc-Trp(Boc)-OH | 614 | 615 | 5.04 (2) |
| 10h | 3-(4-Hydroxy-phenyl)-2-(S)-[2-(8-naphthalen-1-ylmethyl-4-oxo-1-phenyl-1,3,8-triaza-spiro[4.5]dec-3-yl)-acetylamino]-propionamide | Fmoc-Tyr(t-Bu)-OH | 591 | 592 | 4.77 (2) |
| 10i | N-Carbamoylmethyl-2-(8-naphthalen-1-ylmethyl-4-oxo-1-phenyl-1,3,8-triaza-spiro[4.5]dec-3-yl)-acetamide | Fmoc-Gly-OH | 485 | 486 | 4.44 (2) |
| 10j | 2-[2-(8-Naphthalen-1-ylmethyl-4-oxo-1-phenyl-1,3,8-triaza-spiro[4.5]dec-3-yl)-acetylamino]-2-(S)-phenyl-acetamide | Fmoc-Phg-OH | 561 | 562 | 5.47 (2) |

Example 11A

5-Guanidino-2-(S)-{2-[2-(8-naphthalen-1-ylmethyl-4-oxo-1-phenyl-1,3,8-triaza-spiro[4.5]dec-3-yl)-acetylamino]-acetylamino}pentanoic acid amide

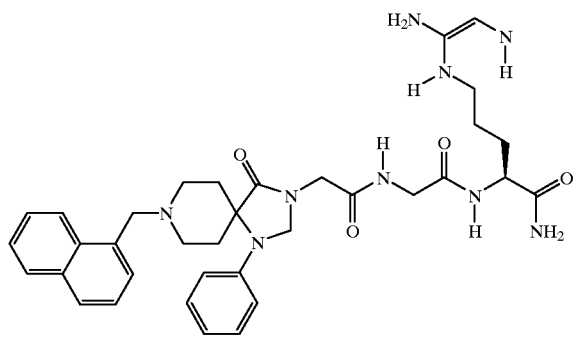

Rink Amide (AM) resin (Novabiochem) (0.200 g, 0.138 mmol) was suspended in dimethylformamide/piperidine (80/20) (8 ml) and shaken for 30 min at room temperature. The resin was filtered and rinsed with dimethylformamide and again suspended in dimethylformamide/piperidine (80/20) (8 ml) and shaken for 30 min at room temperature; the resin was washed as follows: 3×dimethylformamide/water (90/10) (8 ml), 3×dimethylformamide (8 ml), 3×dichloromethane. The resin was suspended in dimethylformamide (8 mL), L-Fmoc-Arg(Pbf)-OH (0.358 g, 0.552 mmol) and 1-hydroxybenzotriazole (0.085 g, 0.552 mmol) were added. N,N'-diisopropylcarbodiimide (0.071 g, 0.552 mmol) was added and the reaction was allowed to shake for 20 h at room temperature. The resin was filtered and washed as follows: 3×dimethylformamide/water (90/10) (8 ml), 3×dimethylformamide (8 ml), 3×dichloromethane (8 ml). The resin was suspended in dimethylformamide/piperidine (80/20) (8 ml) and shaken for 30 min at room temperature. The resin was filtered and rinsed with dimethylformamide and again suspended in dimethylformamide/piperldine (80/20) (8 ml) and shaken for 30 min at room temperature; the resin was washed as follows: 3×dimethylformamide/water (90/10) (8 ml), 3×dimethylformamide (8 ml), 3×dichloromethane (8 ml). The resin was suspended in dimethylformamide (8 ml), Fmoc.Gly.OH (0.163 g, 0.552 mmol), 1-hydroxybenzotriazole (0.085 g, 0.552 mmol) and N,N'-diisopropylcarbodiimide (0.071 g, 0.552 mmol) were added. The reaction was allowed to shake 20 h at room temperature. The resin was filtered and washed as follows: 3×dimethylformamidelwater (80/20) (8 ml), 3×dimethylformamide (8 ml), 3×dichloromethane (8 ml). The resin was suspended in dimethylformamide/piperidine (80/120) (8 ml) and shaken for 30 min at room temperature. The resin was filtered and rinsed with dimethylformamide and again suspended in dimethylformamide/piperidine (80/20) (8 ml) and shaken for 30 min at room temperature; the resin was washed as follows: 3×dimethylformamide/water (90/10) (8 ml), 3×dimethylformamide (8 ml), 3×dichloromethane (8 ml). The resin was suspended in dimethylformamide (8 ml); (8-naphthalen-1-ylmethyl-4-oxo-1-phenyl-1,3,8-triaza-spiro[4.5]dec-3-yl)-acetic acid (0.269 g, 0.552 mmol), 1-hydroxybenzotriazole (0.085 g, 0.552 mmol) and N,N'-diisopropylcarbodiimide (0.071 g, 0.552 mmol) were added. The reaction mixture was allowed to shake at room temperature for 20 h and filtered and washed as follows: 3×dimethylformamide/water (90/10) (8 ml); 3×dimethylformamide (8 ml); 3×dichloromethane (8 ml) and air-dried. The resin was treated with trifluoroacetic acid/water (95/5) (8 ml) for 2 h at room temperature. The filtrate was collected and added dropwise to cyclohexane/ether at 0° C. to form a white precipitate.

The above and following examples were prepared according to this procedure using the appropriate amino acids as outlined in the table below.

| Entry | Name | L-Amino Acids | MW calculated | LCMS MH+ rt(min) (method) |
|---|---|---|---|---|
| 11a | 5-Guanidino-2-(S)-{2-[2-(8-naphthalen-1-ylmethyl-4-oxo-1-phenyl-1,3,8-triaza-spiro[4.5]dec-3-yl)-acetylamino]-acetylamino}-pentanoic acid amide | Fmoc-Arg(Pbf)-OH Fmoc-Gly-OH | 641 | 642 4.07 (2) |
| 11b | 5-Guanidino-2-(S)-(2-{methyl-[2-(8-naphthalen-1-ylmethyl-4-oxo-1-phenyl-1,3,8-triaza-spiro[4.5]dec-3-yl)-acetyl]-amino}-acetylamino)-pentanoic acid amide | Fmoc-Arg(Pbf)-OH Fmoc-Sar-OH | 655 | 656 4.30 (2) |
| 11c | 5-Guanidino-2-(S)-{3-naphthalen-2-yl-2-(S)-[2-(8-naphthalen-1-ylmethyl-4-oxo-1-phenyl-1,3,8-triaza-spiro[4.5]dec-3-yl)-acetylamino]-propionylamino}-pentanoic acid amide | Fmoc-Arg(Pbf)-OH Fmoc-β-(2-naphthyl)-Ala-OH | 781 | 782 4.54 (2) |

Example 12

5-Guanidino-2-(S)-(2-{2-[2-(8-naphthalen-1-ylmethyl-4-oxo-1-phenyl-1,3,8-triaza-spiro[4.5]dec-3-yl)-acetolamino]-acetylamino}-acetylamino)-pentanoic acid amide

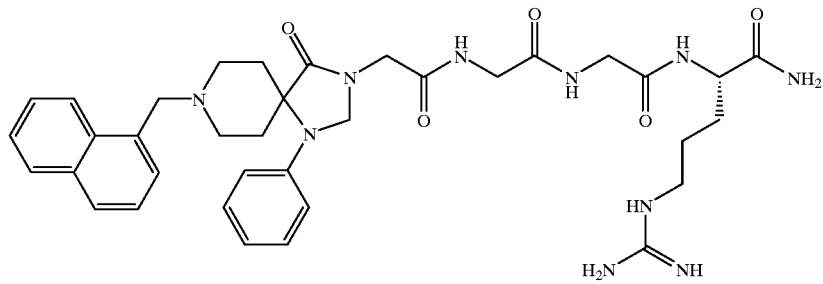

Rink Amide (AM) resin (Novabiochem) (0.200 g, 0.138 mmol) was suspended in dimethylformamide/piperidine (80/20) (8 ml) and shaken for 30 min at room temperature. The resin was filtered and rinsed with dimethylformamide and again suspended in dimethylformamide/piperidine (80/20) (8 ml) and shaken for 30 min at room temperature; the resin was washed as follows: 3×dimethylformamide/water (90/10) (8 ml), 3×dimethylfornamide (8 ml), 3×dichloromethane (8 ml). The resin was suspended in dimethylformamide (8 ml), L-Fmoc-Arg(Pbf)-OH (0.358 g, 0.552 mmol) and 1-hydroxybenzotriazole (0.085 g, 0.552 mmol) were added. N,N'-diisopropylcarbodiimide (0.071 g, 0.552 mmol) was added and the reaction was allowed to shake for 20 h at room temperature. The resin was filtered and washed as follows: 3×dimethylformamide/water (90/10) (8 ml), 3×dimethylformamide (8 ml), 3×dichloromethane (8 ml). The resin was suspended in dimethylformamide/piperidine (80/20) (8 ml) and shaken for 30 min at room temperature. The resin was filtered and rinsed with dimethylformamide and again suspended in dimethylformamide/piperidine (80/20) (8 ml) and shaken for 30 min at room temperature; the resin was washed as follows: 3×dimethylformamide/water (90/10) (8 ml), 3×dimethylformamide (8 ml), 3×dichloromethane (8 ml). The resin was suspended in dimethylformamide (8 ml), Fmoc-Gly-Gly-OH (0.195 g, 0.552 mmol), 1-hydroxybenzotriazole (0.085 g, 0.552 mmol) and N,N'-diisopropylcarbodiimide (0.071 g, 0.552 mmol) were added and the reaction was allowed to shake for 20 h at room temperature. The resin was filtered and washed as follows: 3×dimethylformamide/water (90/10) (8 ml), 3×dimethylformamide (8 ml), 3×dichloromethane (8 ml). The resin was suspended in dimethylformamide/piperidine (80/20) (8 ml) and shaken for 30 min at room temperature. The resin was filtered and rinsed with dimethylformamide and again suspended in dimethylformamide/piperidine (80/20) (8 ml) and shaken for 30 min at room temperature; the resin was washed as follows: 3×dimethylformamide/water (90/10) (8 ml), 3×dimethylformamide (8 ml), 3×dichloromethane (8 ml). The resin was suspended in dimethylformamide (8 ml); (8-naphthalen-1-ylmethyl-4-oxo-1-phenyl-1,3,8-triaza-spiro[4.5]dec3-yl)-acetic acid (0.269 g, 0.552 mmol), 1-hydroxybenzotriazole (0.085 g, 0.552 mmol) and N,N'-diisopropylcarbodiimide (0.071 g, 0.552 mmol) were added. The reaction mixture was allowed to shake at room temperature for 20 h, filtered and washed as follows: 3×dimethylformamide/water (90/10) (8 ml); 3×dimethylformamide (8 ml), 3×dichloromethane (8 ml). The resin was treated with trifluoroacetic acid/water (95/5) (8 ml) for 2 h at room temperature. The filtrate was collected and added dropwise to cyclohexane/diethylether (50/50) at 0° C. to form a white precipitate which was collected and washed with the cyclohexaneldiethylether solution. 32.5 mg of product were collected.

Calculated MW=698, LCMS (method 2), retention time= 4.20 min, MH+=699.

Example 13

3-(7-Aminoheptyl)-8naphthalen-1-ylmethyl-1-phenyl-1,3,8-triaza-spiro[4.5]decan-4-one, ditrifluoroacetate

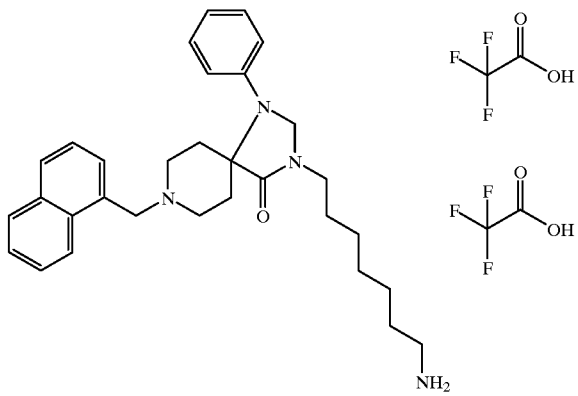

Sodium hydride, 60% (0.156 g, 3.9 mmol) was suspended in dry heptane (5 ml) and stirred under nitrogen for 5 minutes. The solvent was decanted and dry dimethyl formamide (4 ml) was added. 8-Naphthalen-1-ylmethyl-1-phenyl-1,3,8-triazaspiro[4.5]decan-4-one (1.115 g, 3.0 mmol), dissolved in dry dimethyl formamide (11 ml) was added dropwise under cooling in an ice bath. The mixture was stirred at 0° C. for 1 h. The resulting solution of deprotonated 1-phenyl-8-naphthalen-1-ylmethyl-1,3,8-triazaspiro[4.5]decan-4-one was added dropwise to a stirred solution of 1,7-dibromoheptane (3.88 g, 15 mmol) in dimethyl formamide (3 ml) at room temperature and stirring was continued for 1 h. The mixture was then diluted with water (50 ml) and extracted with ethyl acetate (2×30 ml). The combined organic phases were successively washed with water (2×20 ml) and brine (2×20 ml), dried over $MgSO_4$ and evaporated In vacuo. The residue was dissolved in a mixture of tetrahydrofuran (10 ml) and ether (10 ml) and the hydrochloride was precipitated by the dropwise addition of a solution of hydrogen chloride in ether in excess. The precipitate was washed with a 1:1 mixture of tetrahydrofuran and ether and dried, affording 3-(7-bromo-heptyl)-8-naphthalen-1-ylmethyl-1-phenyl-1,3,8-triaza-spiro[4.5]decan-4-one (1.192 g, 68% yield) as a powder.

LC/MS (Method 2): m/e=550.2 (MH+); RT=6.74 min.

1H NMR (200 MHz, $CDCl_3$) d 1.4 (bm, 6H), 1.51–1.9 (m, 6H), 3.3–3.6 (m, 8H), 3.92 (broad dd, 2H), 4.70 (s, 4H), 6.86 (t, 1H), 7.15 (d, 2H), 7.35 (t, 2H), 7.5–7.7 (m, 3H), 7.92 (dd, 2H), 8.15 (d, 1H), 8.38 (d, 1H).

The above bromide (0.38 g, 0.65 mmol) was dissolved in a 5 M ammonia solution in ethanol (7.5 ml) and heated in an autoclave at 100° C. for 16 h. The solution was evaporated in vacuo and the residue was purified by preparative HPLC using a C18-silica column. The column was eluted with a linear gradient of 10–90% acetonitril and 90–10% 0.1% trifluoroacetic acid in 15 minutes. The pure fraction was evaporated in vacuo, dissolved in waterlacetonitrile and freeze dried, to afford the title compound (0.238 g, 51% yield) as a powder.

LC/MS (Method2): m/e=485.4 (MH+); RT=4.77 min

Calculated for $C_{31}H_{40}N_4O$, 2 $CF_3CO_2H$, 0.5 $H_2O$: C, 58.25%; H, 6.00%; N, 7.76%; Found: C, 58.20%; H, 6.13%; N, 7.23%.

The following compounds were synthesized using the above procedure and the appropriate dihaloalkane:

3-(5Aminopentyl)-naphthalen-1-ylmethyl-1-phenyl-1,3,8-triaza-spiro[4.5]decan-4-one, di-trifluoroacetate LC/MS (Method 2): m/e=457.4 (MH+); RT=5.17 min Calculated for $C29H_{36}N_4O$, 2 $CF_3CO_2H$: C, 57.89%; H, 5.59%; N, 8.18%; Found: C, 57.57%; H, 5.54%; N, 8.05%.

3-(9-Aminononyl)-8-naphthalen-1-ylmethyl-1-phenyl-1,3,8-triaza-spiro[4.5]decan-4-one di-trifluoroacetate

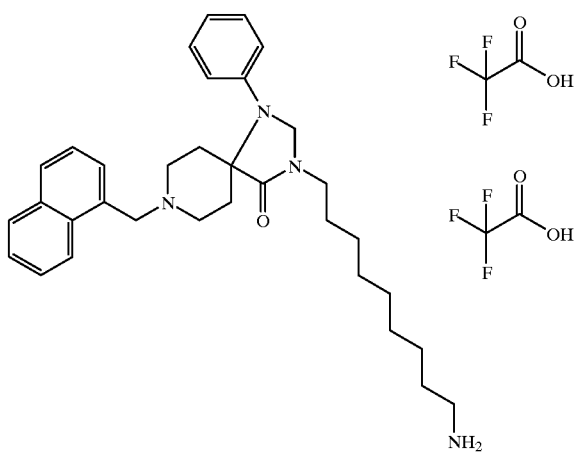

LC/MS (Method 2): m/e=513.6 (MH$^+$); RT=5.03 min

Calculated for $C_{33}H_{44}N_4O$, 2.4 $CF_3CO_2H$: C, 57.73%; H, 5.95%; N, 7.12%; Found: C, 57.75%; H, 6.07%; N, 7.17%.

Example 14

3-(3-Dimethylaminopropyl)-8-naphthalen-1-ylmethyl-1-phenyl-1,3,8-triaza-spiro[4.5]decan-4-one dihydrochloride

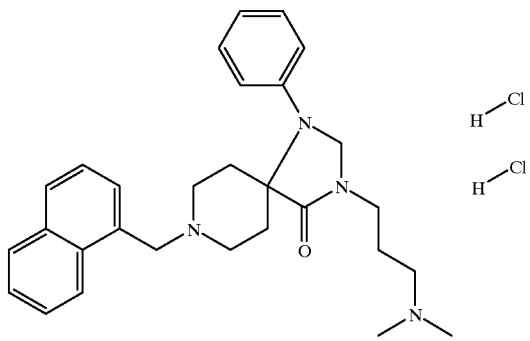

3-(3-chloropropyl)-8-naphthalen-1-ylmethyl-1-phenyl-1,3,8-triaza-spiro[4.5]decan-4-one (0.145 g, 0.30 mmol), prepared using the procedure described in Example 13, was added to a 33% solution of dimethylamine in ethanol. Sodium iodide (0.045 g, 0.3 mmol) was added and the mixture was stirred at room temperature for 24 h. Salts were separated by filtration and the filtrate was evaporated in vacuo. The residue was purified by flash chromatography on silica gel using dichloromethane/ethyl acetate 1:1 containing 2.5% triethylamine as the eluent. The pooled pure fractions were evaporated and the residue dissolved in tetrahydrofuran (5 ml) and the hydrochloride was precipitated by the dropwise addition of a solution of hydrogen chloride in ether in excess. The precipitate was collected by filtration and dried, affording the title compound (148 mg, 93% yield) as a powder.

LC/MS (Method 2): m/e=457.4 (MH$^+$); RT=4.47 min

Calculated for $C_{29}H_{36}N_4O$, 2 HCl, 2 $H_2O$: C, 61.59%; H. 7.48%; N. 9.60%; Found: C, 61.56%; H, 7.23%; N, 9.30%.

The following compound was synthesized using the above procedure.

3-(7-Dimethylaminoheptyl)-8-naphthalen-1-ylmethyl-1-phenyl-1,3,8-triaza-spiro[4.5]decan-4-one dihydrochlonde The compound was synthesized using 3-(7-bromoheptyl)-8-naphthalen-1-ylmethyl-1-phenyl-1,3,8-triaza-spiro[4.5]decan-4-one, prepared as described in Example 13.

LC/MS (Method 2): m/e=513.6 (MH$^+$); RT=4.77 min $^1$H NMR (400 MHz, CDCl$_3$) d 1.4 (m, 6H), 1.65 (m, 2H), 1.74 (d, 2H), 1.87 (m, 2H), 2.80 (s, 6H), 3.35–3.55 (m, 6H), 3.90 (m, 2H), 4.72 (s, 4H), 6.85 (t, 1H), 7.13 (d, 2H), 7.35 (t, 2H), 7.55–7.70 (m, 3H), 7.95 (t, 2H), 8.17 (d, 1 H), 8.33 (d, 1H), 12.4 (broad s, 1H), 12.7 (broad s, 1H).

Example 15

N-(5-(8-Naphthalen-1-ylmethyl-4-oxo-1-phenyl-1,3,8,-triazaspiro[-4.5]dec-3-yl)pentyl)guanidine

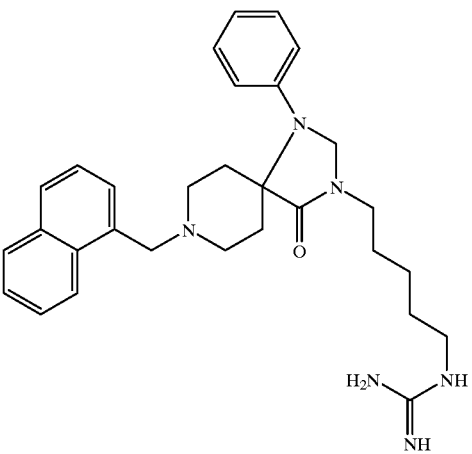

3-(5-Aminopentyl)-8-naphthalen-1-ylmethyl-1-phenyl-1,3,8-triaza-spiro[4.5]decan-4-one, di-trifluoroacetate (0.137 g, 0.2 mmol) prepared as described in Example 13, was dissolved in dimethylformamide (1 ml) and diisopropylethylamine (0.233 g, 1.8 mmol) and 3,5-dimethylpyrazol-1-carboxamidine nitrate (0.060 g, 0.3 mmol) was added. The mixture was stirred at room temperature for 1 h and the addition of an equal amount 3,5-dimethylpyrazol-1 carboxamidine nitrate was repeated. After stirring for 16 h the mixture was diluted with water (10 ml) and extracted with ether (5×10 ml). The aqueous phase and undissolved syrup were extracted with dichloromethane (10 ml), the dichloromethane solution was washed with water (5×10 ml), dried over MgSO$_4$ and concentrated in vacuo, affording the title compound (0.047 g, 5.2%) as an amorphous powder.

LC/MS (Method 2): m/e=499.2 (MH$^+$); RT=4.70 min $^1$H NMR (400 MHz, DMSO-d$_6$) d 1.3 (m, 2H), 1.45–1.65 (m, 7H), 2.48 (m, 1H), 2.32 (m, 4H), 3.09 (t, 2H), 3.35 (t, 2H), 3.95 (s, 2H), 4.68 (s, 2H), 6.79 (t, 1H), 6.88 (d, 2H), 7.23 (t, 2H), 7.50 (d, 2H), 7.59 (dt, 2H), 7.88 (dd, 1H), 7.95 (d, 1H), 8.40 (d, 1H).

The following compound was synthesized using the above procedure:

N-(5-(8-Naphthalen-1-ylmethyl-4-oxo-1-phenyl-1,3,8,-triazaspiro[4.5]dec-3-yl)heptyl)guanidine

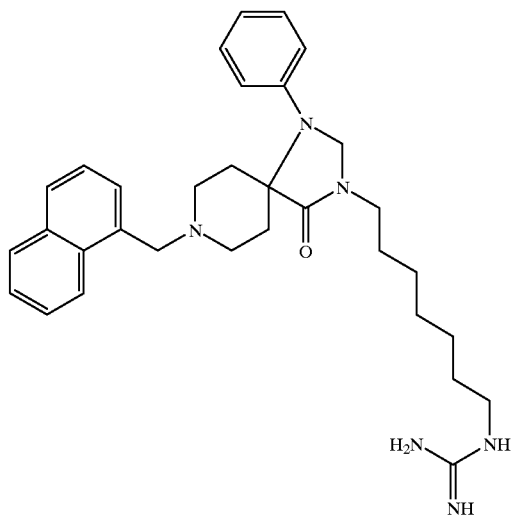

LC/MS (Method 2): m/e=527.2 (MH$^+$); RT=4.90 min
$^1$H NMR (200 MHz, DMSOd$_6$) d 1.2–1.4 (m, 6H), 1.45–1.70 (m, 6H), 2.5–2.9 (m, 6H), 3.15 (m, 2H), 3.35 (t, 2H), 3.95 (s, 2H), 4.62 (s, 2H), 6.80 (m, 3H), 7.23 (t, 2H), 7.30–7.7 (m, 5H), 7.75 (m, 2H), 8.40 (d, 1H).

Example 16

N-(2-Aminoethylk2-(8-naphthalen-1-ylmethyA-oxo-1-phenyl-1,3,8-triazaspiro[4.5]dec-3-yl)-acetamide dihydmochloride

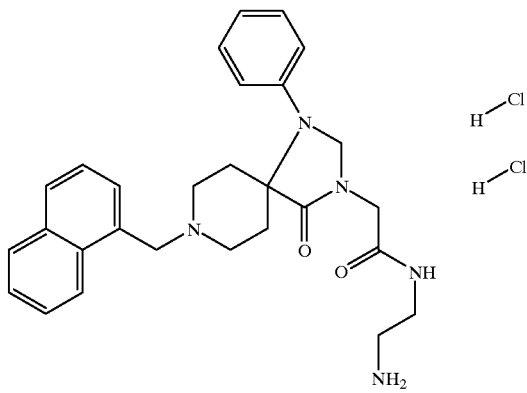

The p-nitrophenylcarbonate derivative of Wang resin was treated with 1,2-diaminoethane according to the procedure described in Tetrahedron Letters, 1995, 36, p. 8677. The resulting resin (2.87 g, 2.5 mmol) was placed in a solid synthesis flask equipped with a glass frit and swelled in dry dimethylformamide (50 ml) for 30 minutes and the excess solvent was removed by suction.

To a suspension of (8-naphthalen-1-ylmethyl-4-oxo-1-phenyl-1,3,8-triaza-spiro[4.5]dec-3-yl)-acetic acid (4.88 g, 10 mmol) in dimethyl formamide (30 ml) in a separate flask was added 1-hydroxybenzotriazol (1.35 g, 10 mmol) and diisopropylcarbodiimide (1.26 g, 10 mmol). The mixture was stirred at room temperature for 1 h and then added to the above resin. Diisopropylamine (1.29 g, 10 mmol) was added and the mixture was agitated on a shaker for 16 h. The solution was removed by suction and the resin was washed with dimethylformamide (2×50 ml), dimethylsulfoxide (2×50 ml), dichloromethane (4×50 ml), methanol (3×50 ml) and dichloromethane (1×50 ml). A 1:1 mixture of dichloromethane/trifluoroacetic acid (25 ml) was added and the resin was agitated for 30 min. The solution was drained and the resin was washed with dichloromethane (2×25 ml). The combined filtrates were concentrated in vacuo and the residue was shaken with dichloromethane (50 ml) and saturated NaHCO$_3$-solution (25 ml). The organic phase was washed with water (20 ml) and brine (20 ml) and concentrated in vacuo. The residue was dissolved in tetrahydrofuran and a solution of hydrogen chloride in ether was added. The formed precipitate was collected by filtration and dried to afford the title compound (0.67 g, 49%) as a powder.

LC/MS (Method 2): m/e=472.2 (MH$^+$); RT=4.27 min

Calculated for C$_{28}$H$_{33}$N$_5$O$_2$, 2 HCl, 3 H$_2$O: C, 56.19%; H, 6.90%; N, 11.70%; Found: C, 56.03%; H, 6.45%; N, 11.34%.

The following compound was synthesized using the above procedure:

N-(3-Aminopropyl)-2-(8-naphthalen-1-ylmethyl-4-oxo-1-phenyl-1,3,8-triazaspiro[4.5]dec-3-yl)-acetamide dihydrochloride

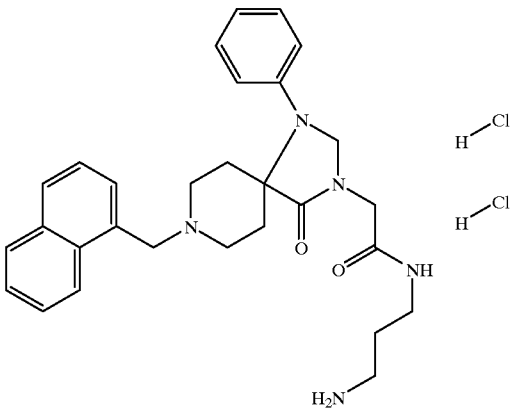

The 1,3-diaminopropyl Wang resin was prepared using the procedure described above.

LC/MS (Method 2): m/e=486.4 (MH$^+$); RT=4.27 min

Calculated for C$_{29}$H$_{35}$N$_5$O$_2$, 2 HCl, 2.75 H$_2$O: C, 57.28%; H, 7.64%; N, 11.52%; Found: C, 57.16%; H, 7.72%; N, 11.20%.

Example 17

N-(2-Guanidinoethyl)-2-(8-naphthalen-1-ylmethylxoxo-1-phenyl-1,3,8,-triazaspiro[4.5]dec-3-yl)-acetamide hydrochloride

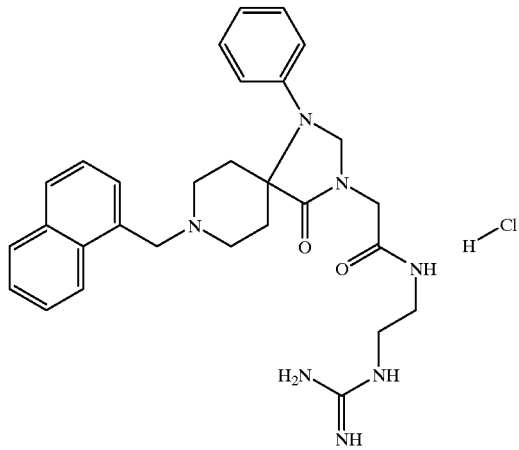

To a solution of N-(2-aminoethyl)2-(8-naphthalen-1-ylmethyl-4-oxo-1-phenyl-1,3,8-triazaspiro[4.5]dec-3yl)-acetamide dihydrochlonde (0.203 g, 0.40 mmol) in dimethylformamide (1.5 ml) was added diisopropylethylamine (0.046 g, 3.6 mmol) and 1-H-pyrazole-1-carboxamidine hydrochloride (0.088 g, 0.60 mmol). The mixture was stirred at room temperature for 1 h and the same amount of 1-H-pyrazole- 1-carboxamidine hydrochloride was added. The reaction was stirred for further 48 h, water (10 ml) was added and the solution was washed with ether (5×10 ml). The aqueous phase was adjusted to pH 1 with diluted hydrochloric acid, washed with dichloromethane (20 ml), adjusted to pH 8 with diluted sodium hydroxide solution and extracted with dichloromethane (3×5 ml). The organic phase was concentrated to 5 ml and left for crystallization in a refrigerator. The precipitate was filtered and dried, affording the title compound (135 mg, 66%) as a powder.

LC/MS (Method 2): m/e=514.4 (MH$^+$); RT=4.37 min

Calculated for $C_{29}H_{35}N_7O_2$, HCl, 0.7 $H_2O$: C, 61.90%; H, 6.70%; N, 17.42%; Found: C, 61.95%; H, 6.52%; N, 17.30%.

Example 18

6-Amino-2-(S)-[2-(S)-{6-amino-2-[2-(8-naphthalen-1-ylmethyl-4-oxo-1-phenyl-1,3,8-triaza-spiro[4.5]dec-3-yl)-acetylamino]-hexanoylamino}acetlamino)-hexanoic acid amide Rink Amide (AM) resin (Novabiochem) (0.200 g, 0.138 mmol) was suspended in dimethylformamide/piperidine (80/20) (8 ml) and shaken for 30 min at room temperature. The resin was filtered and rinsed with dimethylformamide (8 ml) and again suspended in dimethylformamidelpiperidine (80/20) (8 ml) and shaken for 30 min at room temperature; the resin was washed as follows: 3×dimethylformamide/water (90/10) (8 ml), 3×dimethylformamide (8 ml), 3×dichloromethane (8 ml). The resin was suspended in dimethylformamide (8 ml), L Fmoc-Lys(Boc)-OH (0.258 g, 0.552 mmol), 1-hydroxybenzotriazole (0.085 g, 0.552 mmol) and N,N'-diisopropylcarbodiimide (0.071 g, 0.552 mmol) were added and the reaction was allowed to shake for 20 h at room temperature. The resin was filtered and washed as follows: 3×dimethylformamide/water (90/10) (8 ml), 3×dimethylformamide (8 ml), 3×dichloromethane (8 ml). The resin was suspended in dimethylformamide/piperidine (80/20) (8 ml) and shaken for 30 min at room temperature. The resin was filtered and rinsed with dimethylformamide (8 ml) and again suspended in dimethylformamide/piperidine (80/20) (8 ml) and shaken for 30 min at room temperature; the resin was washed as follows: 3×dimethylformamide/water (90/10) (8 ml), 3×dimethylformamide (8 ml), 3×dichloromethane (8 ml). The resin was suspended in dimethylformamide (8 ml); Fmoc-Gly-OH (0.163 g, 0.552 mmol), 1-hydroxybenzotriazole (0.085 g, 0.552 mmol) and N,N'-diisopropylcarbodiimide (0.071 g, 0.552 mmol) were added and the reaction was allowed to shake for 20 h at room temperature. The resin was filtered and washed as follows: 3×dimethylformamidelwater (90/10) (8 ml), 3×dimethylformamide (8 ml), 3×dichloromethane (8 ml). The resin was suspended in dimethylformamidelpiperidine (80/20) (8 ml) and shaken for 30 min at room temperature. The resin was filtered and rinsed with dimethylformamide and again suspended in dimethylformamidelpiperidine (80/20) (8 ml) and shaken for 30 min at room temperature; the resin was washed as follows: 3×dimethylformamide/water (90/10) (8 ml), 3×dimethylformamide (8 ml), 3×dichloromethane (8 ml). The resin was suspended in dimethylformamide (8 ml); L-Fmoc-Lys(Boc)-OH (0.258 g, 0.552 mmol), 1-hydroxybenzotriazole (0.085 g, 0.552 mmol) and N,N'-diisopropylcarbodiimide (0.071 g, 0.552 mmol) were added and the reaction was allowed to shake for 20 h at room temperature. The resin was filtered and washed as follows: 3×dimethylformamide/water (90/10) (8 ml), 3×dimethylformamide (8 ml), 3×dichloromethane (8 ml). The resin was suspended in dimethylformamide/piperidine (80/20) (8 ml) and shaken for 30 min at room temperature. The resin was filtered and rinsed with dimethylformamide (8 ml) and again suspended in dimethylformamidelpiperidine (80/20) (8 ml) and shaken for 30 min at room temperature; the resin was washed as follows: 3×dimethylformamide/water (90/10) (8 ml), 3×dimethylformamide (8 ml), 3×dichloromethane (8 ml). The resin was suspended in

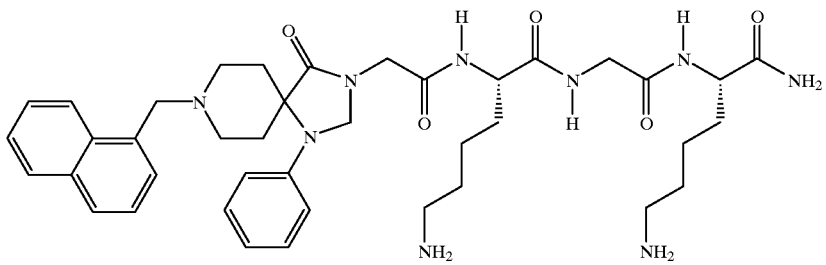

dimethylformamide (8 ml); (8-naphthalen-1-ylmethyl-4-oxo-1-phenyl-1,3,8-triaza-spiro[4.5]dec-3-yl)-acetic acid (0.269 g, 0.552 mmol), 1-hydroxybenzotriazole (0.085 g, 0.552 mmol) and N,N'-diisopropylcarbodiimide (0.071 g, 0.552 mmol) were added. The reaction mixture was allowed to shake at room temperature for 20 h, filtered and washed as follows: 3×dimethylformamide/water (90/10) (8 ml); 3×dimethylformamide; 3×dichloromethane (8 ml). The resin was treated with trifluoroacetic acid/water (95/5) (8 ml) for 2 h at room temperature. The filtrate was collected and added dropwise to heptane/diethylether at 0° C. to form a white precipitate which was collected and washed with the heptane/diethylether solution. 13.7 mg of product were isolated.

Calculated MW=741, LCMS (method 2) shows retention time=3.80 min, MH+=742.

What is claimed is:

1. A compound of formula Ia or Ib:

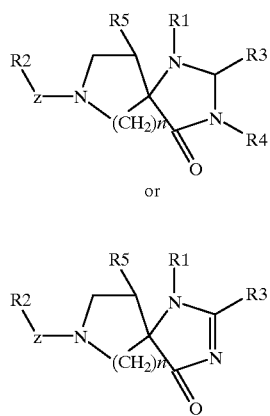

wherein
R$^1$ is C$_{1-6}$-alkyl; or R$^1$ is phenyl, arylalkyl or thienyl, each of which is optionally substituted with halogen, cyano, nitro, trifluoromethyl, C$_{1-6}$-alkyl, hydroxy, C$_{1-6}$-alkoxy or —NR$^6$R$^8$, wherein R$^6$ and R$^8$ are independently hydrogen or C$_{1-6}$-alkyl;
R$^2$ is aminophenyl, C$_{1-6}$-monoalkylaminophenyl, C$_{1-6}$-dialkylaminophenyl, cyanophenyl, C$_{2-6}$-alkylphenyl, naphthyl, anthryl, furanyl, indanyl, benzothienyl, benzofuranyl, coumarinyl, phenyl, phenoxy, benzodioxinyl or cyanodiphenylmethyl, each of which is optionally substituted with halogen, cyano, nitro, trifluoromethyl, C$_{1-6}$-alkyl, hydroxy, C$_{1-6}$-alkoxy or —C(O)R$^7$, wherein R$^7$ is —OH, C$_{1-6}$-alkoxy or —NR$^{12}$R$^{13}$, wherein R$^{12}$ and R$^{13}$ are independently hydrogen or C$_{1-6}$-alkyl;
R$^3$ is hydrogen, C$_{1-6}$-alkyl, phenyl, benzyl or acetyl;
R$^4$ is —(CH$_2$)$_m$—(CHR$^9$)—(CH$_2$)p-AR$^{11}$, wherein A is —(C=O)—, m and p are independently 0 to 4, R$^9$ is hydrogen, C$_{1-6}$-alkyl, phenyl or arylalkyl, and R$^{11}$ is an amino acid residue or a 2 to 4 peptidyl residue with a C-terminal group consisting of either —OCH$_3$ or —NH$_2$;
R$^5$ is hydrogen or C$_{1-4}$-alkyl;
z is —CHR$^{10}$, wherein R$^{10}$ is hydrogen, C$_{1-6}$-alkyl, phenyl, arylalkyl; or z is C$_{2-8}$-alkylene, C$_{2-8}$-alkenylene or C$_{2-8}$-alkynylene; and
n is 2;

or a pharmaceutically acceptable salt thereof.

2. A compound of claim 1 having formula Ia:

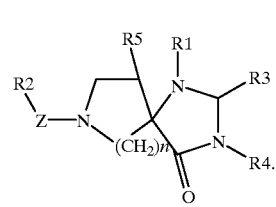

3. A compound of claim 2 wherein R$^3$, R$^9$ and R$^{10}$ are independently hydrogen or C$_{1-6}$-alkyl, and R$^1$ is phenyl optionally substituted with a halogen, cyano, nitro, trifluoromethyl, C$_{1-6}$-alkyl, hydroxy, C$_{1-6}$-alkoxy or —NR$^6$R$^8$.

4. A compound of claim 2 wherein R$^2$ is naphthyl, anthryl, furanyl, indanyl, benzothienyl, benzofuranyl or coumarinyl, each of is which is optionally substituted with halogen, cyano, nitro, trifluoromethyl, C$_{1-6}$-alkyl, hydroxy, C$_{1-6}$-alkoxy or —C(O)R$^7$.

5. A compound of claim 4 wherein R$^2$ is naphthyl, or naphthyl substituted with halogen, cyano, nitro, trifluoromethyl, C$_{1-6}$-alkyl, hydroxy, C$_{1-6}$-alkoxy or —C(O)R$^7$.

6. A compound of claim 5 wherein R$^2$ is 8-naphthalen-1-yl.

7. A compound of claim 2 wherein R$^{11}$ is an amino acid residue.

8. A compound of claim 2 wherein R$^{11}$ is a 2–4 peptidyl residue.

9. A compound of claim 1 which is:
5-Guanidino-2-(S)-[2-(8-naphthalen-1-ylmethyl-4-oxo-phenyl-1,3,8-triaza-spiro[4.5]dec-3-yl)-acetylamino] pentanoic acid methylester,
3-(1H-Imidazol-4-yl)-2-(S)-[2-(8-naphthalen-1-ylmethyl-4-oxo-1-phenyl-1,3,8-triaza-spiro[4.5]dec-3-yl)-acetylamino]-propionamide,
5-Guanidino-2-(S)-[2-(8-naphthalen-1-ylmethyl-4-oxo-1-phenyl-1,3,8-triaza-spiro[4.5]dec-3-yl)-acetylamino]-pentanoic acid amide,
5-Guanidino-2-(R)-[2-(8-naphthalen-1-ylmethyl-4-oxo-1-phenyl-1,3,8-triaza-spiro[4.5]dec-3-yl)-acetylamino]-pentanoic acid amide,
6-Amino-2-(S)-[2-(8-naphthalen-1-ylmethyl-4-oxo-1-phenyl-1,3,8-triaza-spiro[4.5]dec-3-yl)-acetylamino]-hexanoic acid amide,
2-(S)-[2-(8-Naphthalen-1-ylmethyl-4-oxo-1-phenyl-1,3,8-triaza-spiro[4.5]dec-3-yl)-acetylamino]-phenyl-acetamide,
N-Carbamoylmethyl-2-(8-naphthalen-1-ylmethyl-4-oxo-1-phenyl-1,3,8-triaza-spiro[4.5]dec-3-yl)-acetamide,
6-Amino-2-(S)-(2-{6-amino-2-(S)-[2-(8-naphthalen-1-ylmethyl-4-oxo-1-phenyl-1,3,8-triaza-spiro[4.5]dec-3-yl)-acetylamino]-hexanoylamino}-acetylamino)-hexanoic acid amide,
5-Guanidino-2-(S)-{2-[2-(8-naphthalen-1-ylmethyl-4-oxo-1-phenyl-1,3,8-triaza-spiro[4.5]dec-3-yl)-acetylamino]-acetylamino}-pentanoic acid amide,
5-Guanidino-2-(S)-(2-{2-[2-(8-naphthalen-1-ylmethyl-4-oxo-1-phenyl-1,3,8-triaza-spiro[4.5]dec-3-yl)-acetylamino]-acetylamino}-acetylamino)-pentanoic acid amide;

or a pharmaceutically acceptable salt thereof.

10. A pharmaceutical composition comprising an effective amount of a compound of claim 1 together with a pharmaceutically acceptable carrier or diluent.

11. A compound of formula Ia or Ib:

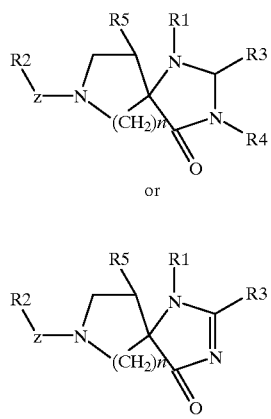

wherein
- $R^1$ is $C_{1-6}$-alkyl; or $R^1$ is phenyl, arylalkyl or thienyl, each of which is optionally substituted with a halogen, cyano, nitro, trifluoromethyl, $C_{1-6}$-alkyl, hydroxy, $C_{1-6}$-alkoxy or —$NR^6R^8$, wherein $R^6$ and $R^8$ are independently hydrogen or $C_{1-6}$-alkyl;
- $R^2$ is aminophenyl, $C_{1-6}$-monoalkylaminophenyl, $C_{1-6}$-dialkylaminophenyl, cyanophenyl, $C_{2-6}$-alkylphenyl, naphthyl, anthryl, furanyl, indanyl, benzothienyl, benzofuranyl or coumarinyl, each of which is optionally substituted with a halogen, cyano, nitro, trifluoromethyl, $C_{1-6}$-alkyl, hydroxy, $C_{1-6}$-alkoxy or —$C(O)R^7$, wherein $R^7$ is —OH, $C_{1-6}$-alkoxy or —$NR^{12}R^{13}$, wherein $R^{12}$ and $R^{13}$ are independently hydrogen or $C_{1-6}$-alkyl;
- $R^3$ is hydrogen, $C_{1-6}$-alkyl, phenyl, benzyl or acetyl;
- $R^4$ is —$(CH_2)_m$—$(CHR^9)$—$(CH_2)p$-$AR^{11}$ wherein, A is —(C=O)—, m and p are independently 0 to 4 and $R^9$ is hydrogen, $C_{1-6}$-alkyl, phenyl or arylalkyl, and $R^{11}$ is hydroxy, $C_{1-6}$-alkoxy, guanidino or —$NR^{14}R^{15}$, wherein $R^{14}$ and $R^{15}$ are independently hydrogen, $C_{1-6}$-alkyl or —$(CH_2)qR^{16}$, wherein q is 0 to 6 and $R^{16}$ is a $C_3$–$C_7$ membered cycloalkyl ring, phenyl, naphthyl, pyrrolidinyl, tetrahydrofuranyl, an alkoxy or aryloxy group, or an amino or a guanidino group;
- $R^5$ is hydrogen or $C_{1-4}$-alkyl;
- z is —$CHR^{10}$, wherein $R^{10}$ is hydrogen, $C_{1-6}$-alkyl, phenyl, arylalkyl; or z is $C_{2-8}$-alkylene, $C_{2-8}$-alkenylene or $C_{2-8}$-alkynylene; and
- n is 2;

or a pharmaceutically acceptable salt thereof.

12. A compound of claim 11 having formula Ia:

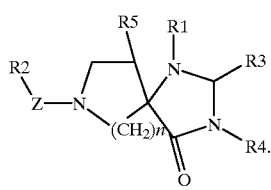

13. A compound of claim 12 wherein $R^3$, $R^9$ and $R^{10}$ are independently hydrogen or $C_{1-6}$-alkyl, and $R^1$ is phenyl optionally substituted with a halogen, cyano, nitro, trifluoromethyl, $C_{1-6}$-alkyl, hydroxy, $C_{1-6}$-alkoxy or —$NR^6R^8$.

14. A compound of claim 12 wherein $R^2$ is $C_{2-6}$-alkylphenyl, naphthyl, anthryl, furanyl, indanyl, benzothienyl, benzofuranyl or coumarinyl, each of which is optionally substituted with a halogen, cyano, nitro, trifluoromethyl, $C_{1-6}$-alkyl, hydroxy, $C_{1-6}$-alkoxy or —C(O)$R^7$.

15. A compound of claim 12 wherein $R^{11}$ is hydroxy or $C_{1-6}$-alkoxy.

16. A compound of claim 12 wherein $R^{11}$ is —$NR^{14}R^{15}$, wherein $R^{14}$ and $R^{15}$ are independently hydrogen or $C_{1-6}$-alkyl.

17. A compound of claim 12 wherein $R^{11}$ is —$(CH_2)qR^{16}$ wherein $R^{16}$ is phenyl, naphthyl, pyrrolidinyl, tetrahydrofuranyl, an alkoxy or aryloxy group, or an amino or a guanidino group.

18. A compound of claim 11 which is:

[4-Oxo-1-phenyl-8-(3-phenyl-propyl)-1,3,8-triaza-spiro[4.5]dec-3-yl]-acetic acid methyl ester,
(8-Naphthalen-1-ylmethyl-4-oxo-1-phenyl-1,3,8-triaza-spiro[4.5]dec-3-yl)-acetic acid methyl ester,
[8-(6,7-Dimethoxy-2-oxo-2H-chromen-4-ylmethyl)-4-oxo-1-phenyl-1,3,8-triaza-spiro[4.5]dec-3-yl]-acetic acid methyl ester,
[8-(2-Naphthalen-1-yl-ethyl)-4-oxo-1-phenyl-1,3,8-triaza-spiro[4.5]dec-3-yl]-acetic acid methyl ester,
3-(3-Methoxycarbonylmethyl-4-oxo-1-phenyl-1,3,8-triaza-spiro[4.5]dec-8-ylmethyl)-benzoic acid methyl ester,
(8-Anthracen-9-ylmethyl-4-oxo-1-phenyl-1,3,8-triaza-spiro[4.5]dec-3-yl)-acetic acid methyl ester,
N-(3-Amino-propyl)-2-(8-naphthalen-1-ylmethyl-4-oxo-1-phenyl-1,3,8-triaza-spiro[4.5]dec-3-yl)-acetamide,
N-(2-Amino-ethyl)-2-(8-naphthalen-1-ylmethyl-4-oxo-1-phenyl-1,3,8-triaza-spiro[4.5]dec-3-yl)-acetamide,
N-(3-Guanidino-propyl)-2-(8-naphthalen-1-ylmethyl-4-oxo-1-phenyl-1,3,8-triaza-spiro[4.5]dec-3-yl)-acetamide,
N-(2-Guanidino-ethyl)-2-(8-naphthalen-1-ylmethyl-4-oxo-1-phenyl-1,3,8-triaza-spiro[4.5]dec-3-yl)-acetamide,
2-(8-Naphthalen-1-ylmethyl-4-oxo-1-phenyl-1,3,8-triaza-spiro[4.5]dec-3-yl)-N-(tetrahydro-furan-2-ylmethyl)-acetamide,
2-(8-Naphthalen-1-ylmethyl-4-oxo-1-phenyl-1,3,8-triaza-spiro[4.5]dec-3-yl)-N-[3-(2-oxo-pyrrolidin-1-yl)-propyl]-acetamide;

or a pharmaceutically acceptable salt thereof.

19. A pharmaceutical composition comprising an effective amount of a compound of claim 11 together with a pharmaceutically acceptable carrier or diluent.

20. A compound of formula Ia or Ib:

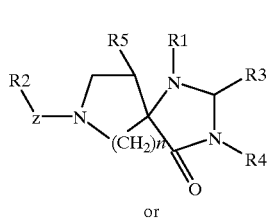

-continued

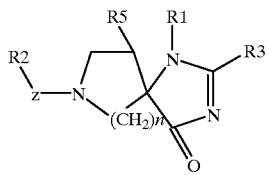

(Ib)

wherein
R[1] is $C_{1-6}$-alkyl; or R[1] is phenyl, arylalkyl or thienyl, each of which is optionally substituted with a halogen, cyano, nitro, trifluoromethyl, $C_{1-6}$-alkyl, hydroxy, $C_{1-6}$-alkoxy or —NR[6]R[8], wherein R[6] and R[8] are independently hydrogen or $C_{1-6}$-alkyl;

R[2] is aminophenyl, $C_{1-6}$-monoalkylaminophenyl, $C_{1-6}$-dialkylaminophenyl, cyanophenyl, naphthyl, furanyl, indanyl or coumarinyl, each of which is optionally substituted with a halogen, cyano, trifluoromethyl, $C_{1-6}$-alkyl, hydroxy, $C_{1-6}$alkoxy or —C(O)R[7], wherein R[7] is —OH, $C_{1-6}$-alkoxy or —NR[12]R[13], wherein R[12] and R[13] are independently hydrogen or $C_{1-6}$-alkyl;

R[3] is hydrogen, $C_{1-6}$-alkyl, phenyl, benzyl or acetyl;

R[4] is —(CH$_2$)$_m$—(CHR[9])—(CH$_2$)p-AR[11] wherein A is —(CH$_2$)—, m and p are independently 0 to 4 and R[9] is hydrogen, $C_{1-6}$-alkyl, phenyl or arylalkyl, and R[11] is $C_{1-6}$-alkyl, hydroxy, $C_{1-6}$-alkoxy, guanidino or —NR[14]R[15], wherein R[14] and R[15] are independently hydrogen, $C_{1-6}$-alkyl or —(CH$_2$)qR[16], wherein q is 0 to 6 and R[16] is a $C_3$–$C_7$ membered cycloalkyl ring, phenyl, naphthyl, pyrrolidinyl, oxo-pyrrolidinyl, tetrahydrofuranyl, an alkoxy or aryloxy group, or an amino or a guanidino group;

R[5] is hydrogen or $C_{1-4}$-alkyl;

z is —CHR[10], wherein R[10] is hydrogen, $C_{1-6}$-alkyl, phenyl, arylalkyl; or z is $C_{2-8}$-alkylene, $C_{2-8}$-alkenylene or $C_{2-8}$-alkynylene; and n is 2;

or a pharmaceutically acceptable salt thereof.

21. A compound of claim 20 having formula Ia:

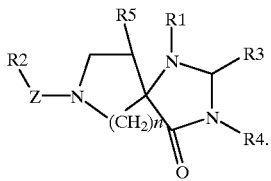

(Ia)

22. A compound of claim 21 wherein R[3], R[9] and R[10] are independently hydrogen or $C_{1-6}$-alkyl, and R[1] is phenyl optionally substituted with a halogen, cyano, nitro, trifluoromethyl, $C_{1-6}$-calkyl, hydroxy, $C_{1-6}$-alkoxy or —NR[6]R[8].

23. A compound of claim 21 wherein R[2] is naphthyl, furanyl, indanyl or coumarinyl, each of which is optionally substituted with a halogen, cyano, trifluoromethyl, $C_{1-6}$-alkyl, hydroxy, $C_{1-6}$-alkoxy or —C(O)R[7].

24. A compound of claim 21 wherein R[4] is —(CH$_2$)$_m$—(CHR[9])—(CH$_2$)p-AR[11], wherein R[11] is $C_{1-6}$-alkyl, hydroxy, $C_{1-6}$-alkoxy, guanidino or —NR[14]R[15], wherein R[14] and R[15] are independently hydrogen, $C_{1-6}$-alkyl or —(CH$_2$)qR[16].

25. A compound of claim 24 wherein R[16] is phenyl, naphthyl, pyrrolidinyl, tetrahydrofuranyl, an alkoxy or aryloxy group, or an amino or a guanidino group.

26. A compound of claim 24 wherein R[11] is $C_{1-6}$-alkyl or guanidino.

27. A compound of claim 24 wherein R[11] is —NR[14]R[15], wherein R[14] and R[15] are independently hydrogen or $C_{1-6}$-alkyl.

28. A compound of claim 21 which is:
3-(7-Amino-heptyl)-8-naphthalen-1-ylmethyl-1-phenyl-1,3,8-triaza-spiro[4.5]decan-4-one,
3-(5-Amino-pentyl)-8aphthalen-1-ylmethyl-1-phenyl-1,3,8-triaza-spiro[4.5]decan-4-one,
N-[7-(8Naphthalen-1-ylmethyl-4-oxo-1-phenyl-1,3,8triaza-spiro[4.5]dec-3-yl)-heptyl]-guanidine,
3-Ethyl-8-naphthalen-1-ylmethyl-1-phenyl-1,3,8-triaza-spiro[4.5]decan-4-one;
or a pharmaceutically acceptable salt thereof.

29. A pharmaceutical composition comprising an effective amount of a compound of claim 20 together with a pharmaceutically acceptable carrier or diluent.

30. A compound of formula Ia or Ib:

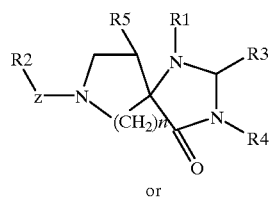

(Ia)

or

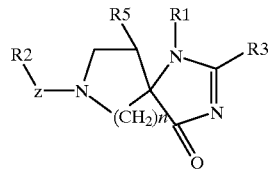

(Ib)

wherein
R[1] is $C_{1-6}$-alkyl; or phenyl, arylalkyl or thienyl, each of which is optionally substituted with halogen, cyano, nitro, trifluoromethyl, $C_{1-6}$-alkyl, hydroxy, $C_{1-6}$-alkoxy or —NR[6]R[8], wherein R[6] and R[8] are independently hydrogen or $C_{1-6}$-alkyl;

R[2] is phenyl optionally substituted with a halogen, cyano, trifluoromethyl, $C_{1-6}$-alkyl, hydroxy, $C_{1-6}$-alkoxy or —C(O)R[7], wherein R[7] is —OH, $C_{1-6}$-alkoxy or —NR[12]R[13], wherein R[12] and R[13] are independently hydrogen or $C_{1-6}$-alkyl;

R[3] is hydrogen, $C_{1-6}$-alkyl, phenyl, benzyl or acetyl;

R[4] is —(CH$_2$)$_m$—(CHR[9])—(CH$_2$)p-AR[11], wherein A is —(C=O)—, m and p are independently 0 to 4 and R[9] is hydrogen, $C_{1-6}$-alkyl, phenyl or arylalkyl, R[11] is hydroxy, $C_{1-6}$-alkoxy, guanidino, an amino acid residue or a 2 to 4 peptidyl residue with a C-terminal group consisting of either —OCH$_3$ or —NH$_2$, or R[11] is —NR[4]R[15] wherein R[14] and R[15] are independently hydrogen, $C_{1-6}$-alkyl or —(CH$_2$)qR[16], wherein q is 0 to 6 and R[16] is a $C_3$–$C_7$ membered cycloalkyl ring, phenyl, naphthyl, pyrrolidinyl, oxo-pyrrolidinyl, tetrahydrofuranyl, an alkoxy or aryloxy group, or an amino or a guanidino group; or R[4] is —(CH$_2$)$_m$—(CHR[9])—(CH$_2$)p-AR[17], wherein A is —(CH$_2$)—, R[17] is guanidino, an amino acid residue or a 2 to 4 peptidyl residue with a C-terminal group consisting of either —OCH$_3$ or —NH$_2$, or R[17] is —NR[14]R[15];

R[5] is hydrogen or $C_{1-4}$-alkyl;

z is —CHR$^{10}$, wherein R$^{10}$ is hydrogen, C$_{1-6}$-alkyl, phenyl, arylalkyl; or z is C$_{2-8}$-alkylene, C$_{2-8}$-alkenylene or C$_{2-8}$-alkynylene; and n is 2;

or a pharmaceutically acceptable salt thereof.

31. A compound of claim 30 having formula Ia:

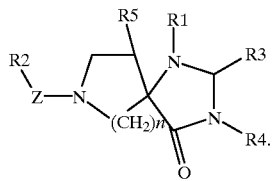

(Ia)

32. A compound of claim 31 having formula Ia wherein R$^3$, R$^9$ and R$^{10}$ are independently hydrogen or C$_{1-6}$-alkyl, and R$^1$ is phenyl optionally substituted with a halogen, cyano, nitro, trifluoromethyl, C$_{1-6}$-alkyl, hydroxy, C$_{1-6}$-alkoxy or —NR$^6$R$^8$.

33. A compound of claim 31 wherein R$^2$ is phenyl optionally substituted with a halogen, cyano, trifluoromethyl, C$_{1-6}$-alkyl, hydroxy or C$_{1-6}$-alkoxy.

34. A compound of claim 31 wherein R$^4$ is —(CH$_2$)$_m$—(CHR$^9$)—(CH$_2$)p-AR$^{11}$, wherein A is —(C=O)—, and R$^{11}$ is C$_{1-6}$-alkyl, hydroxy, C$_{1-6}$-alkoxy, guanidino, an amino acid residue or a 2 to 4 peptidyl residue with a C-terminal group consisting of either —OCH$_3$ or —NH$_2$; or R$^{11}$ is —NR$^{14}$R$^{15}$, wherein R$^{14}$ and R$^{15}$ are independently hydrogen, C$_{1-6}$-alkyl or —(CH$_2$)qR$^{16}$.

35. A compound of claim 31 wherein R$^{16}$ is phenyl, naphthyl, pyrrolidinyl, and tetrahydrofuranyl an alkoxy or aryloxy group, or an amino or a guanidino group.

36. A compound of claim 31 wherein R$^4$ is acetic acid methyl ester.

37. A compound of claim 30 which is:

(4-Oxo-8-phenethyl-1-phenyl-1,3,8-triaza-spiro[4.5]dec-3-yl)-acetic acid methyl ester,

[8-(4-Nitro-benzyl)-4-oxo-1-phenyl-1,3,8-triaza-spiro[4.5]dec-3-yl]-acetic acid methyl ester,

[8-(3-Cyano-benzyl)-4-oxo-1-phenyl-1,3,8-triaza-spiro[4.5]dec-3-yl]-acetic acid methyl ester,

[8-(4-Bromo-benzyl)-4-oxo-1-phenyl-1,3,8-triaza-spiro[4.5]dec-3-yl]-acetic acid methyl ester,

[8-(3,4-Dichloro-benzyl)-4-oxo-1-phenyl-1,3,8-triaza-spiro[4.5]dec-3-yl]-acetic acid methyl ester;

or a pharmaceutically acceptable salt thereof.

38. A pharmaceutical composition comprising an effective amount of a compound of claim 30 together with a pharmaceutically acceptable carrier or diluent.

* * * * *